(12) United States Patent
Ratan

(10) Patent No.: US 9,034,299 B2
(45) Date of Patent: May 19, 2015

(54) ATF4 INHIBITORS AND THEIR USE FOR NEURAL PROTECTION, REPAIR, REGENERATION, AND PLASTICITY

(75) Inventor: Rajiv R. Ratan, Scarsdale, NY (US)

(73) Assignee: Cornell University, Ithaca, NY (US)

( * ) Notice: Subject to any disclaimer, the term of this patent is extended or adjusted under 35 U.S.C. 154(b) by 1049 days.

(21) Appl. No.: 12/672,013

(22) PCT Filed: Aug. 4, 2008

(86) PCT No.: PCT/US2008/009413
§ 371 (c)(1),
(2), (4) Date: Aug. 15, 2011

(87) PCT Pub. No.: WO2009/020601
PCT Pub. Date: Feb. 12, 2009

(65) Prior Publication Data
US 2011/0286927 A1    Nov. 24, 2011

Related U.S. Application Data

(60) Provisional application No. 60/963,558, filed on Aug. 3, 2007.

(51) Int. Cl.
*G01N 33/50* (2006.01)

(52) U.S. Cl.
CPC .... *G01N 33/5058* (2013.01); *G01N 2333/4706* (2013.01)

(58) Field of Classification Search
None
See application file for complete search history.

(56) References Cited

U.S. PATENT DOCUMENTS

| | | |
|---|---|---|
| 2003/0215428 A1 | 11/2003 | Filbin et al. |
| 2004/0019102 A1* | 1/2004 | Kennedy ................ 514/476 |
| 2006/0088535 A1 | 4/2006 | Bartsch et al. |
| 2006/0089335 A1 | 4/2006 | Liu et al. |
| 2006/0104969 A1 | 5/2006 | Oray et al. |
| 2007/0037188 A1 | 2/2007 | Sudhof et al. |
| 2007/0244033 A1 | 10/2007 | Masuda et al. |
| 2007/0298442 A1 | 12/2007 | Liu |
| 2008/0009030 A1 | 1/2008 | Erhardt et al. |
| 2008/0038202 A1 | 2/2008 | Zhao et al. |
| 2008/0044390 A1 | 2/2008 | Ji et al. |

FOREIGN PATENT DOCUMENTS

| | | |
|---|---|---|
| WO | WO2007022478 A2 | 2/2007 |
| WO | WO2007109107 A2 | 9/2007 |

OTHER PUBLICATIONS

Liggan et al., "Some Neurobiological Aspects of Psychoherapy", J. Psychother Pract Res., 8:2, pp. 103-114 (1999).
Siu et al., "ATF4 is a Mediator of the Nutrient-Sensing Response Pathway that Activates the Human Asparagine Synthetase Gene", Journal of Biological Chemistry, vol. 277, No. 27, pp. 24120-24217 (2002).
Ord et al., "Mouse NIPK Interacts with ATF4 and Affects it Transcriptional Activity", Experimental Cell Research 286, pp. 308-320 (2003).
Vaynman et al., "License to Run: Exercise Impacts Functional Plasticity in the Intact and Injured Center Nervous System by using Neurotrophins", Neurorehabilitation and Neural Repair, vol. 19, No. 4, pp. 283-294 (2005).
Hayashi et al., "Molecular Mechanisms of Ischemic Neuronal Cell Death—With relevance to Alzheimer's Disease", Current Alzheimer Research, vol. 3, pp. 351-258 (2006).
Lange et al., "ATF4 is an Oxidative Stree-Inducible, Prodeath Transcription Factor in Neurons in Vitro and in Vivo", The Journal of Experimental Medicine (May 5, 2008).

\* cited by examiner

*Primary Examiner* — Gregory S Emch
*Assistant Examiner* — Adam M Weidner
(74) *Attorney, Agent, or Firm* — Hoffmann & Baron, LLP

(57) ABSTRACT

In one aspect, the invention relates to a method for identifying a drug candidate with activity as a neuroprotective agent. The method includes determining whether a compound reduces ATF4 activity; and identifying the compound that reduces ATF4 activity as a drug candidate.

6 Claims, 47 Drawing Sheets

FIGURE 3
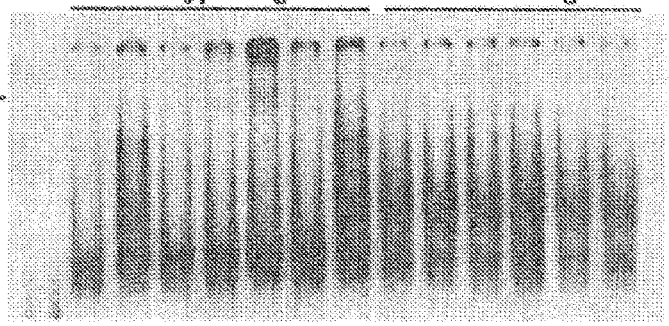
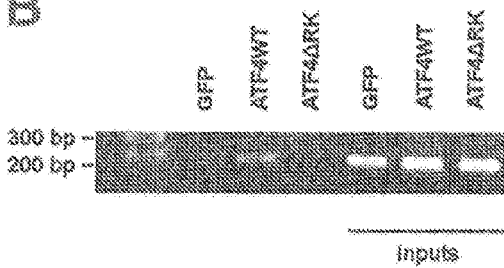
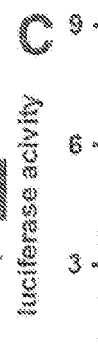
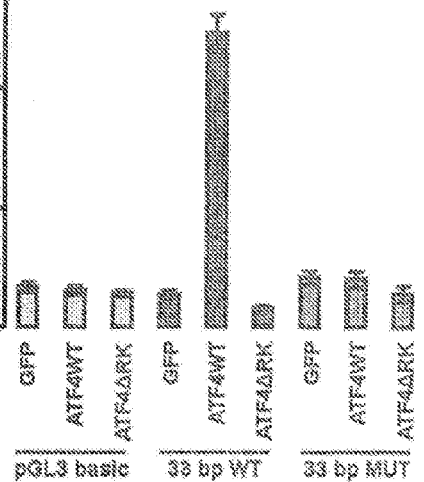

FIGURE 8
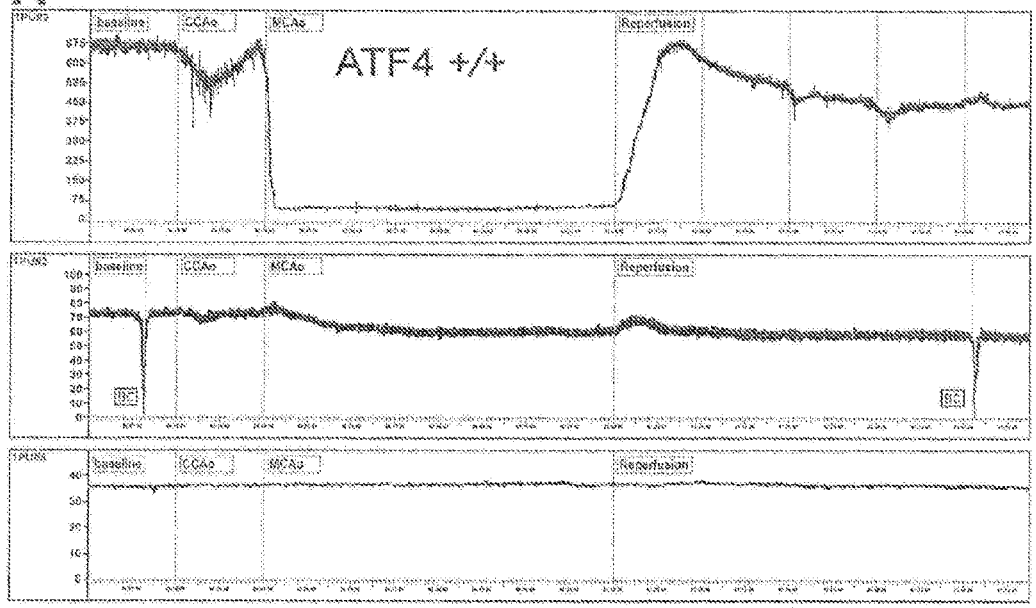
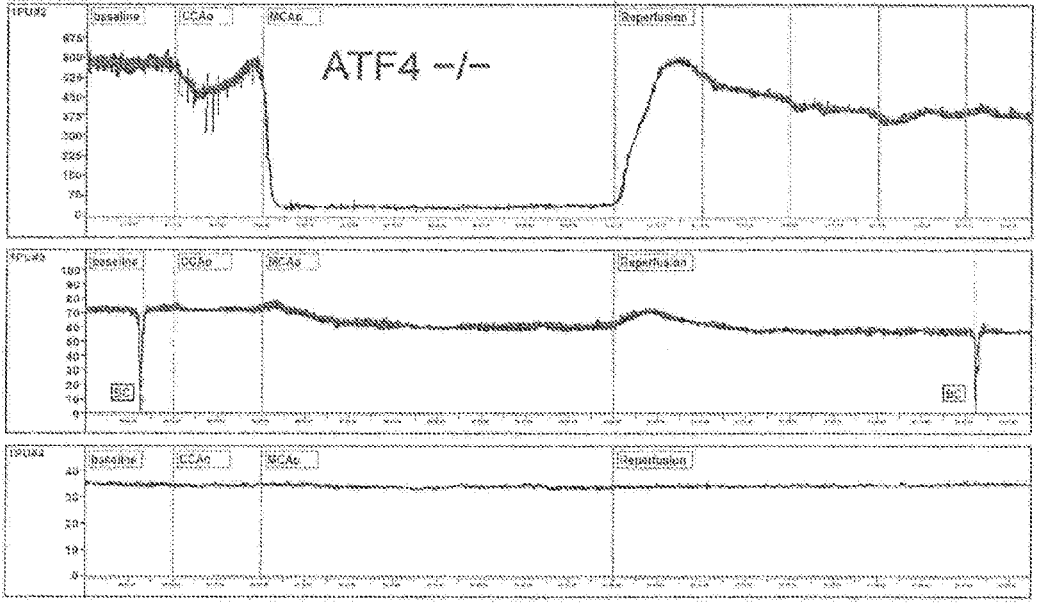

| Product/homology | GenBank | This study | Atf4-/- | | | | Perk-/- | | | |
|---|---|---|---|---|---|---|---|---|---|---|
| | | | Tm % of WT | SD | UT % of WT | SD | Tm % of WT | SD | UT % of WT | SD |
| Translation, amino acid import, and metabolism | | | | | | | | | | |
| Asns — asparagine synthetase | U38940 | x | 14 | 1 | 24 | 4 | 67 | 11 | 58 | 4 |
| EST — alanyl tRNA synthetase homolog | AI839392 | x | 17 | 1 | 42 | 5 | 67 | 7 | 91 | 5 |
| Slc7a5 — cationic amino acid transporter, y+ system | AB017189 | x | 18 | 1 | 40 | 9 | 40 | 18 | 55 | 13 |
| AAAT — neutral amino acid transporter B | L42115 | | 22 | 1 | 63 | 2 | 62 | 0 | 170 | 85 |
| Mthfd2 — methylenetatrahydrofolate dehydrogenase | J04627 | x | 22 | 5 | 36 | 7 | 87 | 21 | 68 | 8 |
| Rpms7 — phosphoserine aminotransferase homolog | AW122030 | x | 25 | 1 | 32 | 2 | 86 | 37 | 85 | 6 |
| EST — L-3-phosphoserine phosphatase homolog | AI846545 | | 27 | 1 | 52 | 10 | 63 | 3 | 63 | 5 |

FIGURE 10B

| | | | | | | | | | | | |
|---|---|---|---|---|---|---|---|---|---|---|---|
| PHAS-I; eIF4Ebp1 | eukaryotic translation initiation regulator | U28656 | x | 27 | 2 | 46 | 1 | 59 | 15 | 64 | 0 |
| Nars | asparaginyl-tRNA synthetase | AW125874 | x | 27 | 1 | 40 | 4 | 52 | 7 | 69 | 14 |
| WRS | tryptophan-tRNA synthetase | X69656 | | 31 | 2 | 44 | 19 | 10 | 3 | 43 | 13 |
| meca39; Bcat1 | branched chain aminotransferase 1 | U42443 | x | 32 | 3 | 46 | 7 | 53 | 15 | 66 | 33 |
| EST | threonyl-tRNA synthetase homolog | AI849620 | | 32 | 6 | 45 | 7 | 58 | 24 | 74 | 11 |
| EST | leucyl-tRNA synthetase homolog | AI844089 | | 33 | 0 | 55 | 9 | 50 | 3 | 68 | 11 |
| Slc3a2 | 4F2 antigen heavy chain, amino acid transporter | X14309 | x | 35 | 2 | 63 | 14 | 86 | 23 | 82 | 8 |
| EST | SYY-Tyrosyl tRNA synthetase homolog | AW122542 | | 40 | 2 | 64 | 3 | 70 | 2 | 89 | 7 |
| EST | isoleucine-tRNA synthetase homolog | AI848393 | | 45 | 0 | 52 | 8 | 83 | 5 | 89 | 14 |
| Redox or detoxification | | | | | | | | | | | |
| EST | NADH-cytochrome B5 reductase homolog | AI839690 | | 18 | 1 | 43 | 1 | 19 | 4 | 47 | 14 |
| Cpo | coproporphyrinogen oxidase (hem6) | D16333 | | 32 | 2 | 82 | 39 | 31 | 1 | 47 | 22 |
| Ero1i-pending | ERO1 like, oxidoreductase | AA798624 | | 36 | 1 | 63 | 16 | 57 | 6 | 77 | 24 |
| EST | FKBP13/PDI homolog | AW122851 | | 39 | 6 | 25 | 0 | 81 | 2 | 75 | 0 |

FIGURE 10C

| | | | | | | | | | | | |
|---|---|---|---|---|---|---|---|---|---|---|---|
| HO-1, Gmox1 | heme oxygenase | X56824 | x | 45 | 2 | 65 | 5 | 67 | 3 | 69 | 5 |
| Transcription | | | | | | | | | | | |
| C/EBPBeta | CCAAT/enhancer binding protein, Beta | M61007 | x | 15 | 4 | 31 | 2 | 29 | 7 | 51 | 17 |
| Prx2 | homeo box of paired rule | X52875 | x | 32 | 2 | 22 | 2 | 52 | 2 | 59 | 6 |
| C/EBRGamma | GPE1-BP (C/EBPGamma) | AB012273 | | 48 | 5 | 65 | 12 | 41 | 2 | 85 | 26 |
| Secreted or transmembrane protein | | | | | | | | | | | |
| ptx3 | pentaxin related gene | X83601 | | 7 | 1 | 31 | 14 | 10 | 1 | 32 | 10 |
| Lgals3, L-34 | galactoside-binding lectin; IgE binding protein | X16834 | | 15 | 1 | 18 | 11 | 238 | 120 | 207 | 148 |
| EST | coagulation factor XIIIa homolog | AI839918 | | 19 | 1 | 46 | 8 | 50 | 12 | 71 | 1 |
| X11Gamma | X11gamma protein, mint3, APBA3, Mint-3 | AF070975 | x | 33 | 2 | 46 | 3 | 58 | 3 | 99 | 17 |
| PMP22 | Peripheral myelin protein | Z38110 | x | 37 | 3 | 40 | 1 | 102 | 52 | 52 | 10 |
| Nid2, Ly111 | Nidogen 2; entactin-2 | AB017202 | x | 41 | 14 | 38 | 9 | 154 | 15 | 57 | 10 |
| Signalling | | | | | | | | | | | |
| IGFBP-2 | insulin-like growth factor | X81580 | | 7 | 0 | 9 | 1 | 13 | 7 | 12 | 2 |

FIGURE 10D

| | binding protein-2 | | | | | | | | | | |
|---|---|---|---|---|---|---|---|---|---|---|---|
| Osmr | Oncostatin M receptor beta | AB015978 | | 26 | 9 | 28 | 9 | 23 | 6 | 66 | 16 |
| EST | EST, GTP-binding protein homolog | AA867773 | | 36 | 6 | 60 | 0 | 88 | 16 | 100 | 10 |
| OPG; Tnfrsf11b | osteoprotegerin, TGFbeta family | U94331 | | 39 | 2 | 42 | 13 | 37 | 4 | 38 | 10 |
| Arhj | Ras homolog gene family | AW121127 | | 44 | 2 | 53 | 4 | 20 | 12 | 19 | 4 |
| Wisp1 | WNT1 inducible signaling pathway protein 1 | AF100777 | x | 46 | 0 | 97 | 11 | 21 | 2 | 27 | 8 |
| Grb10 | growth factor receptor binding protein | U18996 | | 47 | 5 | 50 | 13 | 70 | 8 | 71 | 12 |
| Miscellaneous | | | | | | | | | | | |
| Lon | Lon mitochondrial protease homolog | AI838015 | | 2 | 1 | 104 | 109 | 27 | 3 | 195 | 174 |
| PEDF, Serpinf11 | serpin-f1 pigment epithelium-derived factor | AF036164 | x | 10 | 1 | 20 | 3 | 29 | 1 | 37 | 1 |
| Gys | muscle glycogen synthase | U53218 | | 43 | 0 | 50 | 0 | 44 | 3 | 56 | 4 |
| Clic4 | chloride intracellular channel 4 (mitochondrial) | AI849533 | x | 46 | 1 | 70 | 13 | 62 | 3 | 46 | 10 |
| MIBP-1 | myc-intron-binding protein-1 | Y15907 | | 47 | 0 | 69 | 8 | 24 | 33 | 56 | 12 |

FIGURE 11

|  |  | WT | KO |
|---|---|---|---|
| before MCAo |  |  |  |
| pO2 | mmHg | 101.33 ± 3.51 | 101.33 ± 2.08 |
| pCO2 | mmHg | 35.33 ± 0.58 | 33.67 ± 0.58 |
| pH |  | 7.44 ± 0.02 | 7.39 ± 0.02 |
| $HCO_3^-$ | mmol/l | 22.61 ± 1.28 | 21.84 ± 0.42 |
| Glucose | mg/dl | 87.94 ± 3.78 | 90.38 ± 1.7 |
| Lactate | mmol/l | 1.20 ± 0.11 | 1.2 ± 0.07 |
| mABP |  | 73.95 ± 2.56 | 72.95 ± 2.94 |
| mT | °C | 36.01 ± 0.19 | 35.61 ± 0.4 |
| after MCAo |  |  |  |
| pO2 | mmHg | 97.67 ± 1.53 | 96.67 ± 0.58 |
| pCO2 | mmHg | 32.33 ± 1.53 | 33.67 ± 1.15 |
| pH |  | 7.39 ± 0.02 | 7.38 ± 0.03 |
| $HCO_3^-$ | mmol/l | 20.59 ± 0.66 | 20.66 ± 0.57 |
| Glucose | mg/dl | 86.58 ± 5.03 | 85.28 ± 1.05 |
| Lactate | mmol/l | 1.21 ± 0.05 | 1.19 ± 0.05 |
| mABP |  | 67.38 ± 2.71 | 66.31 ± 1.11 |
| mT | °C | 35.49 ± 0.37 | 35.61 ± 0.41 |

FIGURE 12A

| ID | Molename | Structure | FORMULA | MWt | atf4 inhibition | Therap cat: | Source |
|---|---|---|---|---|---|---|---|
| 01500572 | Thimerosal | 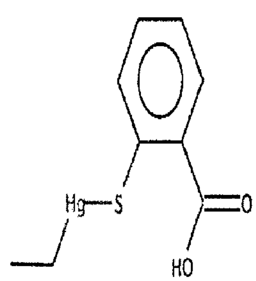 | C9H9HgNaO2S | 404.8 | 98.7 | Anti-infective, preservative | |

FIGURE 12B
| 00200007 | Gambogic Acid | 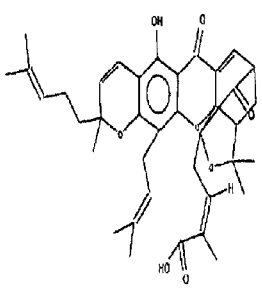 | C38H44O8 | 628.8 | 98.7 | antiinflammatory agent | ex gamboge resin |
|---|---|---|---|---|---|---|---|
| 00100005 | Anthothecol | 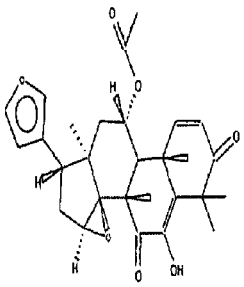 | C28H32O7 | 480.6 | 98.4 | | |

FIGURE 12C

| 01500262 | Disulfiram | | C10H20N2S4 | 296.5 | 98.3 | Alcohol deterrent | |
|---|---|---|---|---|---|---|---|
| 01500260 | Pyrithione Zinc | | C10H10N2O2S2Zn | 319.7 | 98.1 | antibacterial; antifungal; antiseborrheic | |

FIGURE 12D

| 01503322 | Thiram | | C6H12N2S4 | 240.4 | 98.0 | antifungal | |
|---|---|---|---|---|---|---|---|
| 01504079 | Tomatine | | C47H79NO21 | 994.1 | 96.0 | antifungal, antibacterial, antiinflammatory agent | ex Solanum spp. |

FIGURE 12E
| 00201524 | Dihydrogambogic Acid | | C38H46O8 | 630.8 | 96.0 | | derivative |
|---|---|---|---|---|---|---|---|
| | | 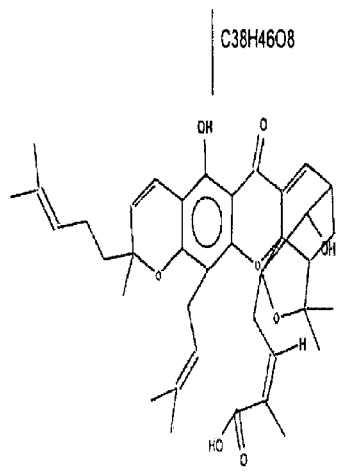 | | | | | |
| 01500591 | Trifluoperazine Hydrochloride | | C21H26Cl2F3N3S | 480.4 | 94.7 | antipsychotic | |
| | | 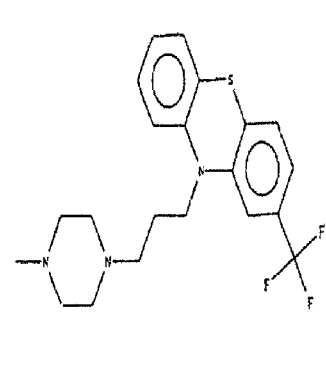 | | | | | |

FIGURE 12F
| 01503074 | Alexidine Hydrochloride | | C26H58Cl2N10 | 581.7 | 92.4 | antibacterial | |
|---|---|---|---|---|---|---|---|
| | | 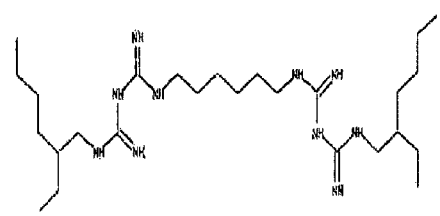 | | | | | |
| 01500644 | Phenylmercuric Acetate | | C8H8HgO2 | 336.7 | 92.0 | fungicide | |
| | | 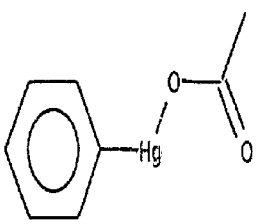 | | | | | |

FIGURE 12G
| 1504181 | Pristimerin | | C30H40O4 | 464.7 | 90.9 | antineoplastic, antinflammatory; | Celastrus and Maytenus spp |
|---|---|---|---|---|---|---|---|
| | | 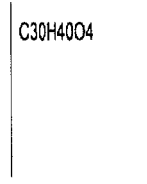 | | | | | |
| 00200022 | Aklavine Hydrochloride | | C30H36ClNO10 | 606.1 | 88.8 | antibiotic of the e-isorhodomycin group; antineoplastic | exActinomyces spp |
| | | 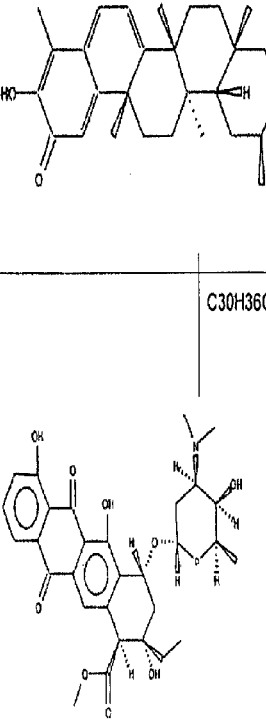 | | | | | |

FIGURE 12H
| 01504132 | 6,3'-Dimethoxyflavone | 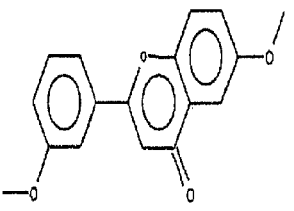 | C17H14O4 | 282.3 | 88.5 | | Pimelia decora |
|---|---|---|---|---|---|---|---|
| 01504101 | Tetrachloroisophthalonitrile | 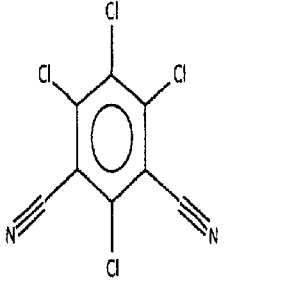 | C8Cl4N2 | 265.9 | 87.5 | fungicide | |

FIGURE 12I
| 00330001 | Actinomycin D | 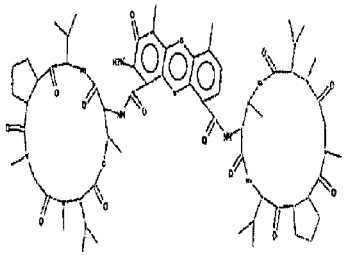 | C64H88N10O16 | 1253.5 | 85.5 | antineoplastic; intercalating agent | exActinomyces spp |
|---|---|---|---|---|---|---|---|
| 00100009 | Cedrelone | 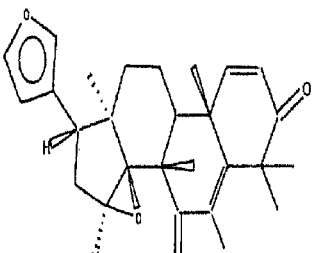 | C26H30O5 | 422.5 | 85.1 | | Cedrela species |

FIGURE 12J
| 00201604 | Pyrromycin | 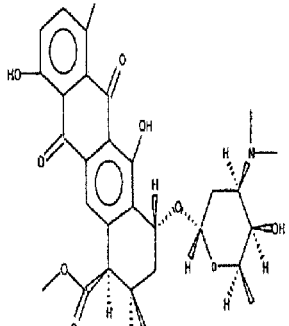 | C30H35NO11 | 585.6 | 83.9 | antibacterial | Streptomyces spp |
|---|---|---|---|---|---|---|---|
| 01503278 | Mitoxanthrone Hydrochloride | 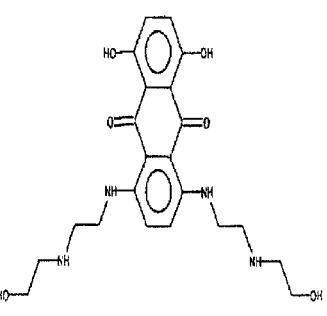 | C22H30Cl2N4O6 | 517.4 | 81.9 | antineoplastic | |

FIGURE 12K
| 01500603 | Tyrothricin | 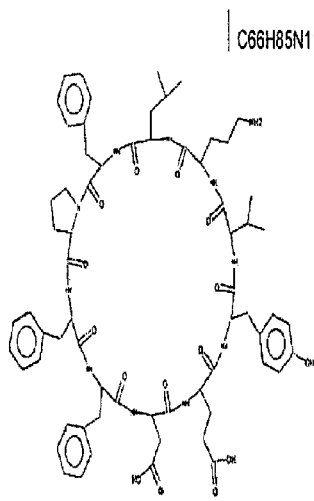 | C66H85N11O15 | 1272.5 | 73.2 | Topical antibacterial | |
|---|---|---|---|---|---|---|---|
| 01504159 | Selinidin | 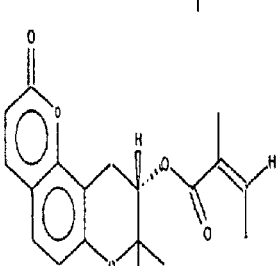 | C19H20O5 | 328.4 | 67.5 | | Selinium vaginatum |

FIGURE 12L
| 01500315 | Gentian Violet | 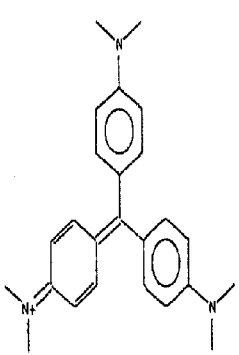 | C25H30ClN3 | 408.0 | 67.3 | Antibacterial: anthelmintic (Nematodes) | |
| --- | --- | --- | --- | --- | --- | --- | --- |
| 01503206 | Clofoctol | 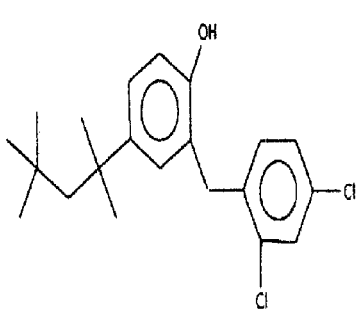 | C21H26Cl2O | 365.3 | 67.1 | antibacterial | |

FIGURE 12M
| 01500810 | Aminacrine | 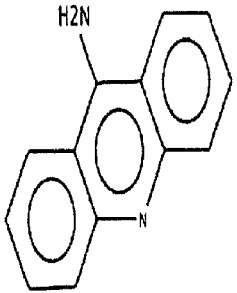 | C13H10N2 | 194.2 | 66.8 | local antiseptic | |
|---|---|---|---|---|---|---|---|
| 01800177 | Penicillic Acid | 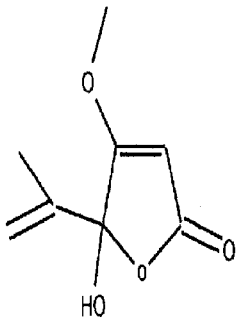 | C8H10O4 | 170.2 | 66.5 | | penicillium spp |

FIGURE 12N
| 01800172 | Byssochlamic Acid | 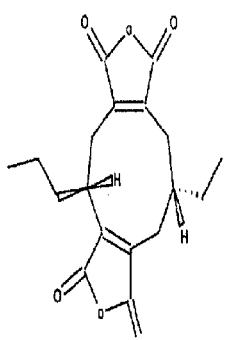 | C18H20O6 | 332.4 | 66.5 | | ex Byssochlamys spp. |
|---|---|---|---|---|---|---|---|
| 01504115 | Hieracin | 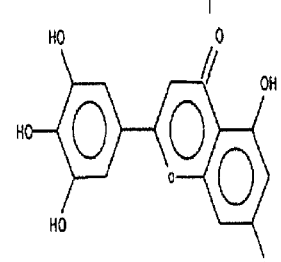 | C15H10O7 | 302.2 | 66.1 | | Ginkgo biloba |

FIGURE 12O

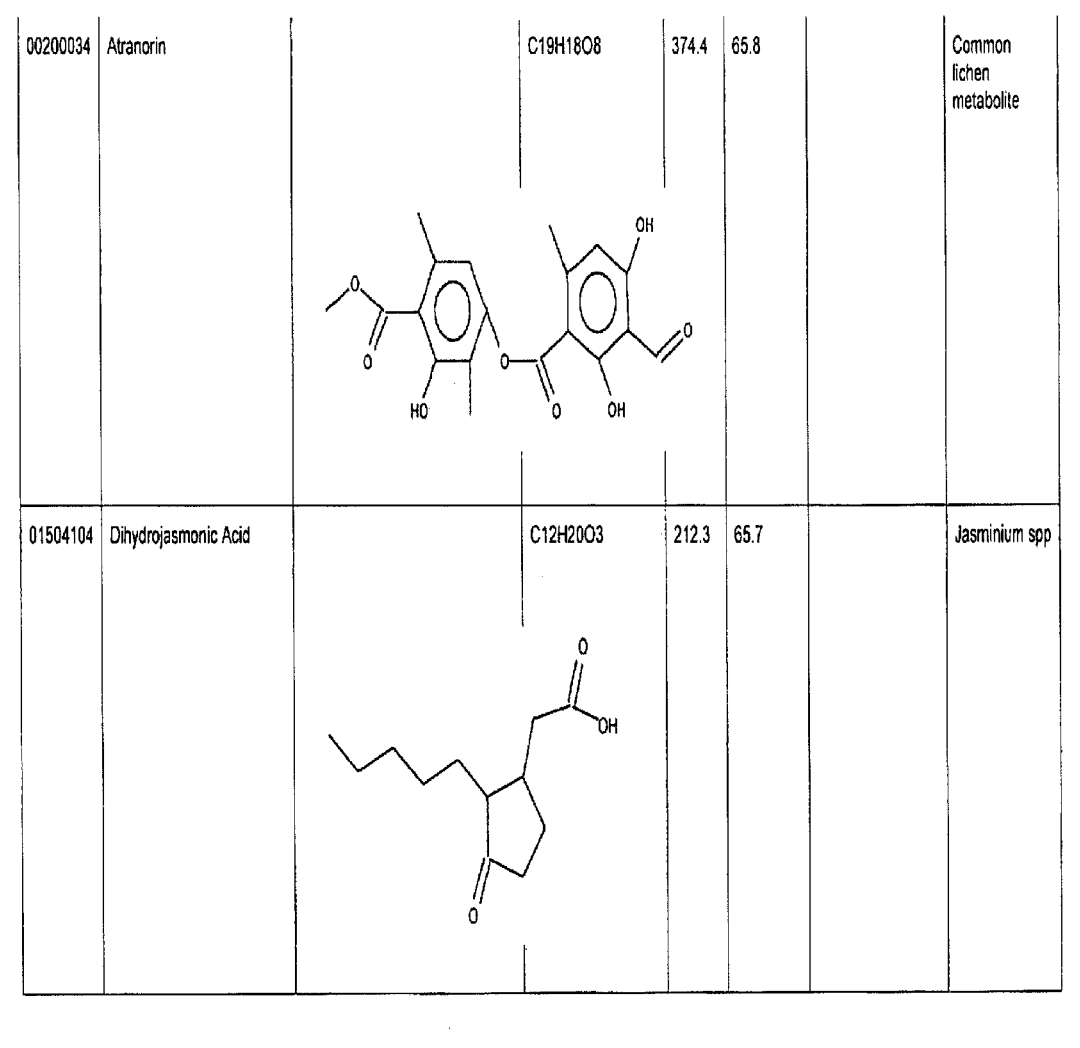

| 00200034 | Atranorin | | C19H18O8 | 374.4 | 65.8 | | Common lichen metabolite |
|---|---|---|---|---|---|---|---|
| 01504104 | Dihydrojasmonic Acid | | C12H20O3 | 212.3 | 65.7 | | Jasminium spp |

FIGURE 12P

| 01504205 | Deltaline | | C24H37NO7 | 451.6 | 65.3 | antiarrhythmic | ex Delphinium spp |
|---|---|---|---|---|---|---|---|
| 01502113 | Azaserine | | C5H7N3O4 | 173.1 | 64.7 | antineoplastic; amino acid antagonist, inhibits protein & nucleic acid synthesis | ex Streptomyces fragilis |

FIGURE 12Q

| | | | | | | |
|---|---|---|---|---|---|---|
| 00330009 | Sodium Fluoroacetate | | C2H2FNaO2 | 100.0 | 64.1 | inhibits the citric acid cycle by formation of fluorocitrate which inhibits aconitase |
| 01503607 | Thalidomide | | C13H10N2O4 | 258.2 | 64.1 | hypnotic |

FIGURE 12R
| 01500427 | Neomycin Sulfate | 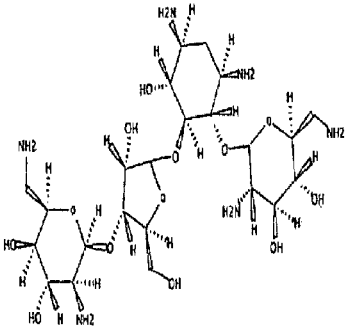 | C23H48N6O17S | 712.7 | 63.5 | Antibacterial | |
|---|---|---|---|---|---|---|---|
| 01502232 | Camptothecin | 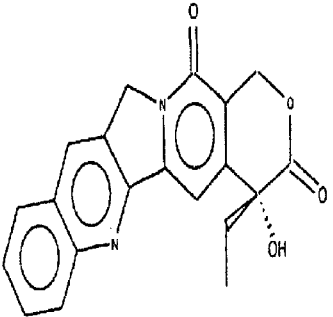 | C20H16N2O4 | 348.4 | 62.3 | antineoplastic | ex Camptotheca acuminata |

FIGURE 12S
| 01504135 | Trimedlure (5-Cl Isomer Present) |  | C12H21ClO2 | 232.8 | 61.2 | arthropod pheromone | |
|---|---|---|---|---|---|---|---|
| 01504211 | Chlorguanide Hydrochloride | 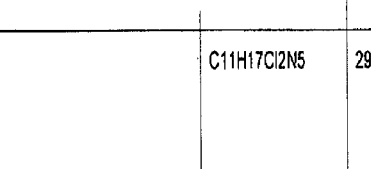 | C11H17Cl2N5 | 290.2 | 59.6 | antimalarial | |

FIGURE 12T
| 00330005 | Benzo[a]pyrene | 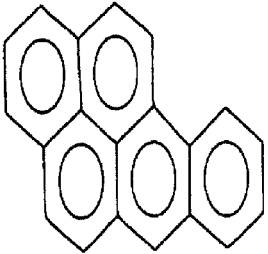 | C20H12 | 252.3 | 59.1 | carcinogen | |
| --- | --- | --- | --- | --- | --- | --- | --- |
| 01503239 | Hycanthone | 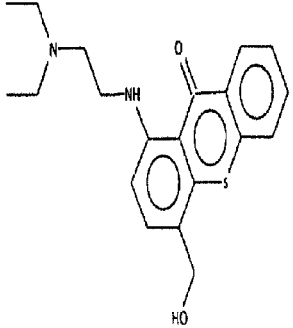 | C20H24N2O2S | 356.5 | 58.0 | anthelmintic, hepatotoxic | |

FIGURE 12U

| 01500398 | Methotrexate | | C20H22N8O5 | 454.4 | 57.7 | Antineoplastic; antirheumaticfolic acid antagonist | |
|---|---|---|---|---|---|---|---|
| 00201449 | Dihydrorotenone | | C23H24O6 | 396.4 | 57.0 | | |

FIGURE 12V
| 01501202 | Galanthamine Hydrobromide | 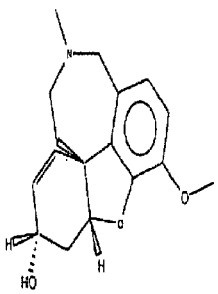 | C17H22BrNO3 | 368.3 | 57.0 | cholinesterase inhibitor, analgesic anti-Alzheimer | ex Galanthus, Narcissus and other Lillaceae |
|---|---|---|---|---|---|---|---|
| 01400010 | Ipraflavone | 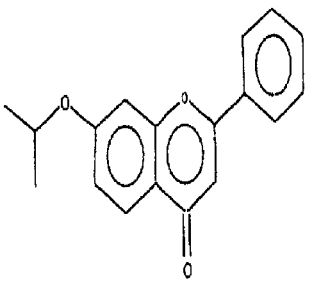 | C18H16O3 | 280.3 | 57.0 | anabolic | |

FIGURE 12W
| 01502062 | 5,7-Dichlorokynurenic Acid | 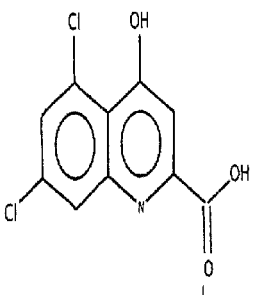 | C10H5Cl2NO3 | 258.1 | 56.5 | NMDA receptor antagonist (gly site) | |
|---|---|---|---|---|---|---|---|
| 00700024 | Haematoporphyrin Dihydrochloride | 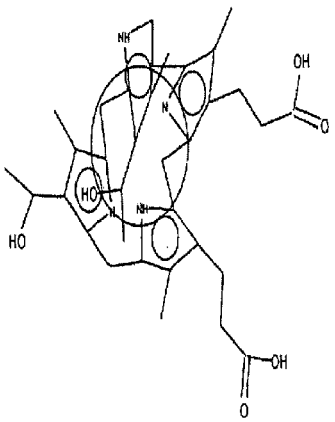 | C34H40Cl2N4O6 | 671.6 | 56.3 | antidepressant | Chlorella vulgaris; derived blood |

FIGURE 12X
| 01504165 | Osthol | 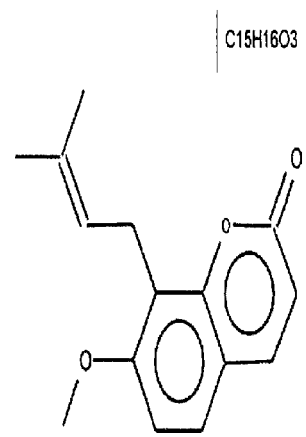 | C15H16O3 | 244.3 | 56.3 | | Imperatoria ostruthium & other Umbelliferae |
|---|---|---|---|---|---|---|---|
| 02300253 | 1r,2s-Phenylpropylamine | 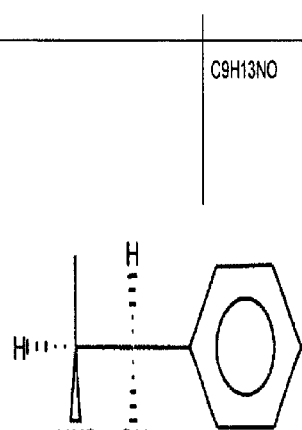 | C9H13NO | 151.2 | 56.3 | decongestant | ex Ephedra vulgaris (MaHuang) |

FIGURE 12Y

| 00330008 | 2,4-Dinitrophenol | | C6H4N2O5 | 184.1 | 56.2 | uncouples oxidative phosphorylation | |
|---|---|---|---|---|---|---|---|
| 01503108 | Bromopride | | C14H22BrN3O2 | 344.3 | 56.2 | antiemetic | |

FIGURE 12Z
| 00200015 | Isorotenone | | C23H22O6 | 394.4 | 55.8 | | |
|---|---|---|---|---|---|---|---|
| | | 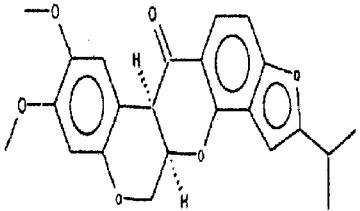 | | | | | |
| 00100279 | Lycorine | | C16H17NO4 | 287.3 | 55.3 | | Amarylidaceae spp |
| | | 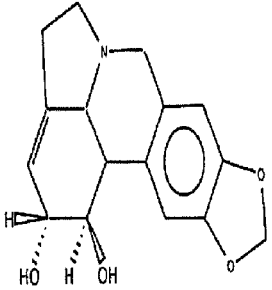 | | | | | |

FIGURE 12AA

| 01503237 | Halcinonide | | C24H32ClFO5 | 455.0 | 54.9 | glucocorticoid, antiinflammatory | |
|---|---|---|---|---|---|---|---|
| 00100146 | 7-Desacetoxy-6,7-Dehydrogedunin | | C26H30O5 | 422.5 | 54.7 | | derivative of gedunin |

FIGURE 12AB
| 01505315 | 6-Aminonicotinamide | 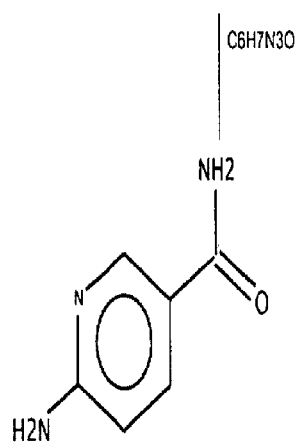 | C6H7N3O | 137.1 | 54.3 | antineoplastic, apotosis inducer | |
|---|---|---|---|---|---|---|---|
| 01503254 | 6alpha-methylprednisolone acetate | 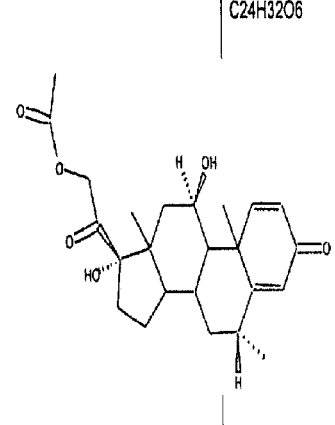 | C24H32O6 | 416.5 | 53.5 | glucocorticoid | |

FIGURE 12AC
| 01504094 | Teniposide | | C32H32O13S | 656.7 | 53.5 | antineoplastic | |
|---|---|---|---|---|---|---|---|
| | | 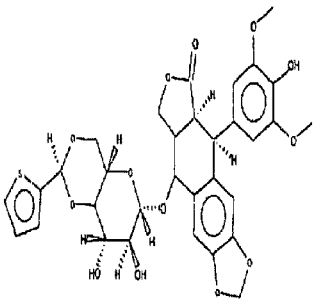 | | | | | |
| 02300329 | 1-Methylxanthine | | C6H6N4O2 | 166.1 | 53.5 | | major component of human urine; weak diuretic &adenosine antagonist |
| | | 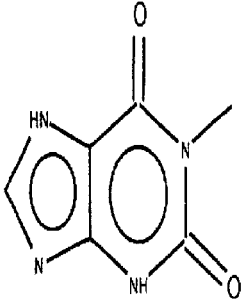 | | | | | |

FIGURE 12AD
| 01500387 | Mercaptopurine | 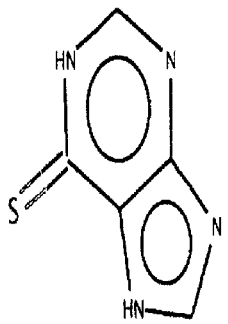 | C5H4N4S | 152.2 | 53.2 | Antineoplastic; purine antimetabolite: inhibits nucleic acid replication | |
| 01500597 | Tripelennamine Citrate | 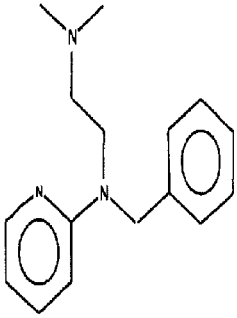 | C22H29N3O7 | 447.5 | 53.1 | Antihistaminic | |

FIGURE 12AE

| 02300104 | 9-Amino-1,2,3,4-Tetrahydroacridine Hydrochloride | | C13H15ClN2 | 234.7 | 52.9 | anticholinesterase; K-channel blocker |
|---|---|---|---|---|---|---|
| 00201153 | Beta-Dihydrorotenone | | C23H24O6 | 396.4 | 51.5 | |

FIGURE 12 AF

| 01502002 | Acivicin | | C5H7ClN2O3 | 178.6 | 51.1 | antineoplastic | ex Streptomyces civiceus |
|---|---|---|---|---|---|---|---|
| 02300100 | Hydroxytacrine Maleate | | C17H18N2O5 | 330.3 | 50.4 | Cholinesterase inhibitor; antiparkinsonian | |

| 01500169 | Cetylpyridinium Chloride | | C21H38ClN | 340.0 | 47.6 | Topical anti-infective | |

SEQUENCE LISTING

<160> NUMBER OF SEQ ID NOS: 15

<210> SEQ ID NO 1
<211> LENGTH: 24
<212> TYPE: DNA
<213> ORGANISM: Artificial Sequence
<220> FEATURE:
<223> OTHER INFORMATION: synthetic nucleotide sequence

<400> SEQUENCE: 1
agcaaaacaa gacagcagcc acta                                          24

<210> SEQ ID NO 2
<211> LENGTH: 23
<212> TYPE: DNA
<213> ORGANISM: Artificial Sequence
<220> FEATURE:
<223> OTHER INFORMATION: synthetic nucleotide sequence

<400> SEQUENCE: 2
atattgctga agagcttggc ggc                                           23

<210> SEQ ID NO 3
<211> LENGTH: 27
<212> TYPE: DNA
<213> ORGANISM: Artificial Sequence
<220> FEATURE:
<223> OTHER INFORMATION: synthetic nucleotide sequence

<400> SEQUENCE: 3
gtttctacag cttcctcctc cactctt                                27

<210> SEQ ID NO 4
<211> LENGTH: 25
<212> TYPE: DNA
<213> ORGANISM: Artificial Sequence
<220> FEATURE:
<223> OTHER INFORMATION: Synthetic nucleotide sequence

<400> SEQUENCE: 4
ctcactcagg tgcctgtagt gctcg                                  25

<210> SEQ ID NO 5
<211> LENGTH: 25
<212> TYPE: DNA
<213> ORGANISM: Artificial Sequence
<220> FEATURE:
<223> OTHER INFORMATION: Synthetic nucleotide sequence

<400> SEQUENCE: 5
tcagcagaag cagccagagg tgtag                                  25

<210> SEQ ID NO 6
<211> LENGTH: 29
<212> TYPE: DNA
<213> ORGANISM: Artificial Sequence
<220> FEATURE:
<223> OTHER INFORMATION: Synthetic nucleotide sequence

<400> SEQUENCE: 6
acactcgaga gagaaacaaa tgtgtcatg                              29

<210> SEQ ID NO 7
<211> LENGTH: 29
<212> TYPE: DNA
<213> ORGANISM: Artificial Sequence
<220> FEATURE:
<223> OTHER INFORMATION: Synthetic nucleotide sequence

<400> SEQUENCE: 7
acaaagcttc tagagagcaa ggaagaaag                              29

<210> SEQ ID NO 8
<211> LENGTH: 45
<212> TYPE: DNA
<213> ORGANISM: Artificial Sequence
<220> FEATURE:
<223> OTHER INFORMATION: Synthetic nucleotide sequence

<400> SEQUENCE: 8
tcgaggcaga ttagctcagg tttacatcag ccgggcgggg atcca            45

<210> SEQ ID NO 9
<211> LENGTH: 45
<212> TYPE: DNA
<213> ORGANISM: Artificial Sequence
<220> FEATURE:

<223> OTHER INFORMATION: Synthetic nucleotide sequence

<400> SEQUENCE: 9
agcttggatc cccgcccggc tgatgtaaac ctgagctaat ctgcc    45

<210> SEQ ID NO 10
<211> LENGTH: 45
<212> TYPE: DNA
<213> ORGANISM: Artificial Sequence
<220> FEATURE:
<223> OTHER INFORMATION: Synthetic nucleotide sequence

<400> SEQUENCE: 10
tcgaggcaga ttagctcagt ctaaacctat aggggcgggg atcca    45

<210> SEQ ID NO 11
<211> LENGTH: 45
<212> TYPE: DNA
<213> ORGANISM: Artificial Sequence
<220> FEATURE:
<223> OTHER INFORMATION: Synthetic nucleotide sequence

<400> SEQUENCE: 11
agcttggatc cccgccccta taggtttaga ctgagctaat ctgcc    45

<210> SEQ ID NO 12
<211> LENGTH: 33
<212> TYPE: DNA
<213> ORGANISM: Artificial Sequence
<220> FEATURE:
<223> OTHER INFORMATION: Synthetic nucleotide sequence

<400> SEQUENCE: 12
gattagctca ggtttacatc agccgggcgg gga    33

<210> SEQ ID NO 13
<211> LENGTH: 33
<212> TYPE: DNA
<213> ORGANISM: Artificial Sequence
<220> FEATURE:
<223> OTHER INFORMATION: Synthethic nucleotide sequence

<400> SEQUENCE: 13
gattagctca gtctaaacct atagggggcgg gga    33

<210> SEQ ID NO 14
<211> LENGTH: 20
<212> TYPE: DNA
<213> ORGANISM: Artificial Sequence
<220> FEATURE:
<223> OTHER INFORMATION: Synthetic nucleotide sequence

<400> SEQUENCE: 14
ggtcacagat ggtgcaatcc    20

<210> SEQ ID NO 15
<211> LENGTH: 21
<212> TYPE: DNA
<213> ORGANISM: Artificial Sequence
<220> FEATURE:
<223> OTHER INFORMATION: Synthetic nucleotide sequence

<400> SEQUENCE: 15
aactgagcag ctctcggagt c    21

ATF4 INHIBITORS AND THEIR USE FOR NEURAL PROTECTION, REPAIR, REGENERATION, AND PLASTICITY

CROSS REFERENCE TO RELATED APPLICATION

This application claims the benefit of U.S. Provisional Application No. 60/963,558, filed Aug. 3, 2007, which is incorporated herein by reference in its entirety.

The invention was made with funds from the W.M. Burke Foundation, by a grant from the National Institutes of Health to Rajiv R. Ratan (NS40591), and by the Dr. Miriam and Sheldon G. Adelson Medical Research Foundation. The invention was also made with funds from a postdoctoral fellowship from the Deutsche Forschungsgemeinschaft (LA 1483/1-1) for Philipp S. Lange and the Koeln Fortune Program/Faculty of Medicine, University of Cologne (125/2003) for Philipp S. Lange. The invention was also made with funds from a Scientist Development Grant for Juan C. Chavez from the Northeast Affiliate of the American Heart Association (0635556T).

BACKGROUND OF THE INVENTION

Neurological disorders affect a wide variety of cell populations in the nervous system. Acute and chronic neurological disorders may be associated with loss of sensory, motor, and cognitive abilities, as well as a high level of mortality. Despite their devastating effects, few effective therapies are available for the vast majority of these disorders.

Neural cell death and loss of neuronal contacts are pathological features common to many of the neurological disorders. Once destroyed, neural cells are not regenerative. Accordingly, there is a long felt need for methods for neural protection, repair, regeneration, and plasticity.

SUMMARY OF THE INVENTION

The present invention addresses these needs, among others. In one aspect, the invention relates to a method for identifying a drug candidate with activity as a neuroprotective agent. The method includes determining whether a compound reduces ATF4 activity, and identifying the compound that reduces ATF4 activity as a drug candidate.

In another aspect, the invention relates to a method for reducing ATF4 activity in a neural cell in a human in need thereof. The method includes administering to the human an effective amount of: Thimerosal; Gambogic Acid; Anthothecol; Disulfuram; Pyrithione Zinc; Thiram; Tomatine; Dihydrogambogic Acid; Trifluoperazine Hydrochloride; Alexidine Hydrochloride; Phenylmercuric Acetate; Pristimerin; Aklavine Hydrochloride; 6,3'-Dimethoxyflavone; Tetrachloroisophthalonitrile; Actinomycin D; Cedrelone; Pyrromycin; Mitoxanthrone Hydrochloride; Tyrothricin; Selinidin; Gentian Violet; Clofoctol; Aminacrine; Penicillic Acid; Byssochlamic Acid; Hieracin; Atranorin; Dihydrojasmonic Acid; Deltaline; Azaserine; Sodium Fluoroacetate; Thalidomide; Neomycin Sulfate; Camptothecin; Trimedlure (5-Cl Isomer Present); Chlorguanide Hydrochloride; Benzo[a]pyrene; Hycanthone; Methotrexate; Dihydrorotenone; Galanthamine Hydrobromide; Ipraflavone; 5,7-Dichlorokynurenic Acid; Haematoporphyrin Dihydrochloride; Osthol; 1r,2s-Phenylpropylamine; 2,4-Dinitrophenol; Bromopride; Isorotenone; Lycorine; Halcinonide; 7-Desacetoxy-6,7-Dehydrogedunin; 6-Aminonicotinamide; 6alpha-methylprednisolone acetate; Teniposide; 1-Methylxanthine; Mercaptopurine; Tripelennamine Citrate; 9-Amino-1,2,3,4-Tetrahydroacridine Hydrochloride; Beta-Dihydrorotenone; Acivicin; Hydroxytacrine Maleate; or Cetylpyridinium Chloride.

In yet another aspect, the invention relates to a method for protecting a neural cell from further neural cell injury or death in a human who has suffered neural cell injury or death. The method includes administering to the human an effective amount of a compound that reduces ATF4 activity.

In a further aspect, the invention relates to a method for promoting recovery of neural cell function in a human that has suffered neural cell injury or death. The method includes administering to the human an effective amount of a compound that reduces ATF4 activity.

In yet a further aspect, the invention relates to a method for promoting synaptic plasticity in a human in need thereof. The method comprises administering to a human in need thereof an effective amount of a compound that reduces ATF4 activity.

In another aspect, the invention relates to a method for limiting oxidative stress in a human who has a condition in which oxidative stress is a mediator of injury. The method includes administering to the human an effective amount of a compound that reduces ATF4 activity.

BRIEF DESCRIPTION OF THE DRAWINGS

FIG. 3. ATF4 binds to a 33-bp binding element within the TRB3 promoter. (A) EMSA performed with 10 µg of dialyzed nuclear extracts from HT22 cells transfected with ATF4WT, mutant ATF4 (ATF4ΔRK), or GFP, respectively. Extracts were incubated with a radioactively labeled WT oligonucleotide containing the TRB3 promoter binding site or with a mutant oligonucleotide. Binding of ATF4WT to the TRB3WT promoter binding site was confirmed by supershift analysis (arrow) performed with an antibody (Ab) directed against ATF4. (B) Overexpressed ATF4WT protein occupies its putative binding site within the TRB3 promoter in HT22 cells, as shown by chromatin immunoprecipitation assay. HT22 cells were transfected with ATF4WT, mutant ATF4 (ATF4ΔRK), or GFP. An anti-myc antibody was used to precipitate the proteins in nuclear extracts of cross-linked HT22 cells. Coprecipitated DNA fragments were detected using PCR with a set of primers specific for the ATF4 binding site in the TRB3 promoter, yielding a 190-bp product. A representative example of three experiments is shown. (C) HT22 cells were transfected with the expression plasmids for ATF4WT, mutant ATF4 (ATF4ΔRK), or GFP. The cells were cotransfected with either a luciferase reporter vector containing the 33-bp ATF4WT binding site (33 by WT), a reporter vector containing a mutant form of this binding site (33 by MUT), or empty vector (pGL3 basic). In parallel, the transfection mix contained a plasmid expressing Renilla to allow normalization for transfection efficiency. The value for empty pGL3 cotransfected with GFP was arbitrarily defined as 1. Shown are ratios of luciferase and Renilla activities (mean±SD for three independent experiments; each data point was performed in duplicate).

FIG. 8. Cerebral blood flow, mean arterial blood pressure, and rectal temperature after MCAo. Local cerebral blood flow (arbitrary values) was monitored in ATF4$^{+/+}$ (A) and ATF4$^{-/-}$ (B) mice before, during MCAo, and after reperfusion by laser Doppler flowmetry. Mean arterial blood pressure (mmHg) was measured by cannulation of the left femoral artery. Rectal temperature (° C.) was measured using a rectal probe. BC, blood sample collection; CCAo, common carotid artery occlusion.

Figure 9:
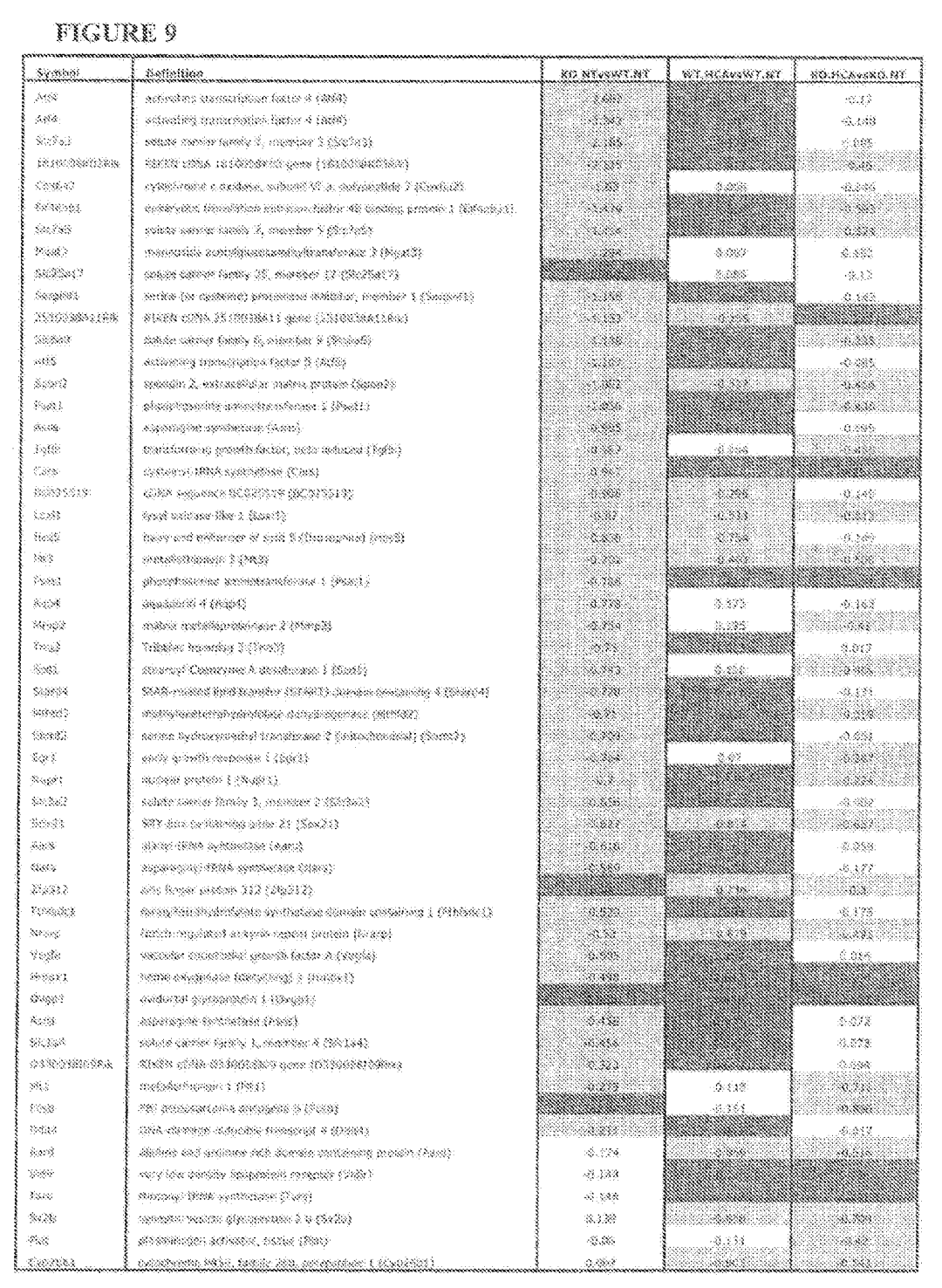

FIG. 9. Differentially expressed genes in ATF4−/− neurons versus ATF4+/+ neurons before and after HCA treatment. From each of the three contrasts, the top 30 genes with the highest fold change were selected. Ratios are log 2 transformed. Up-regulated genes (fold change>0.2) are highlighted in light grey, and down-regulated genes (fold change<−0.2) are highlighted in dark grey.

FIG. 10A. Comparison of the gene array data from this study with array data obtained from ATF4-deficient fibroblasts. An x indicates that the respective gene appears in both datasets as differentially expressed. 42 genes were extracted in the fibroblast array, of which 18 overlap with this study. These are 43% of the 42 genes of the fibroblast data resulting in a high level of significance at the hypergeometric test (P<0.00001). Genes shown in this view include genes related to translation, amino acid import and metabolism.

FIG. 10B. Comparison of the gene array data obtained from ATF4-deficient fibroblasts. An x indicates that the respective gene appears in both datasets as differentially expressed. Genes shown in this view include genes related to translation, amino acid import, metabolism, redox and detoxification.

FIG. 10C. Comparison of the gene array data obtained from ATF4-deficient fibroblasts. An x indicates that the respective gene appears in both datasets as differentially expressed. Genes shown in this view include genes related to redox and detoxification, transcription, secreted, and transmembrane protein and signaling.

FIG. 10D. Comparison of the gene array data obtained from ATF4-deficient fibroblasts. An x indicates that the respective gene appears in both datasets as differentially expressed. Genes shown in this view include genes related to signaling.

FIG. 11. Physiological data from ATF4+/+ and ATF4−/− mice. Shown are the values for blood gases, pH, levels of bicarbonate, glucose, and lactate, and values for mean arterial blood pressure and body temperature. Measurements were carried out 45 min before and after MCAo for three animals each.

FIG. 12B. Chemical structures of Gambogic Acid and Anthothecol,

FIG. 12C. Chemical structures of Disulfiram and Pyrithione Zinc,

FIG. 12D. Chemical structures of Thiram and Tomatine,

FIG. 12E. Chemical structures of Dihydrogambogic Acid and Trifluoperazine Hydrochloride, FIG. 12F. Chemical structures of Alexidine Hydrochloride and Phenylmercuric Acetate, FIG. 12G. Chemical structures of Pristimerin and Aklavine Hydrochloride, FIG. 12H. Chemical structures of 6,3'-Dimethoxyflavone and Tetrachloroisophthalonitrile, FIG. 12I. Chemical structures of Actinomycin D and Cedrelone, FIG. 12J. Chemical structures of Pyrromycin and Mitoxanthrone Hydrochloride, FIG. 12K. Chemical structures of Tyrothricin and Selinidin, FIG. 12L. Chemical structures of Gentian Violet and Clofoctol, FIG. 12M. Chemical structures of Aminacrine and Penicillic Acid, FIG. 12N. Chemical structures of Byssochlamic Acid and Hieracin, FIG. 12O. Chemical structures of Atranorin and Dihydrojasmonic Acid, FIG. 12P. Chemical structures of Deltaline and Azaserine, FIG. 12Q. Chemical structures of Sodium Fluoroacetate and Thalidomide, FIG. 12R. Chemical structures of Neomycin Sulfate and Camptothecin, FIG. 12S. Chemical structures of Trimedlure (5-Cl Isomer Present) and Chlorguanide Hydrochloride, FIG. 12T. Chemical structures of Benzo[a]pyrene and Hycanthone, FIG. 12U. Chemical structures of Methotrexate and Dihydrorotenone, FIG. 12V. Chemical structures of Galanthamine Hydrobromide and Ipraflavone, FIG. 12W. Chemical structures of 5,7-Dichlorokynurenic Acid and Haematoporphyrin Dihydrochloride, FIG. 12X. Chemical structures of Osthol and 1r,2s-Phenylpropylamine, FIG. 12Y. Chemical structures of 2,4-Dinitrophenol and Bromopride, FIG. 12Z. Chemical structures of Isorotenone and Lycorine, FIG. 12AA. Chemical structures of Halcinonide and 7-Desacetoxy-6,7-Dehydrogedunin, FIG. 12AB. Chemical structures of 6-Aminonicotinamide and 6alpha-methylprednisolone acetate, FIG. 12AC. Chemical structures of Teniposide and 1-Methylxanthine, FIG. 12AD. Chemical structures of Mercaptopurine and Tripelennamine Citrate, FIG. 12AE. Chemical structures of 9-Amino-1,2,3,4-Tetrahydroacridine Hydrochloride and Beta-Dihydrorotenone, FIG. 12AF. Chemical structures of Acivicin and Hydroxytacrine Maleate, FIG. 12AG. Chemical structure of and Cetylpyridinium Chloride.

DETAILED DESCRIPTION OF THE INVENTION

Figure 1:
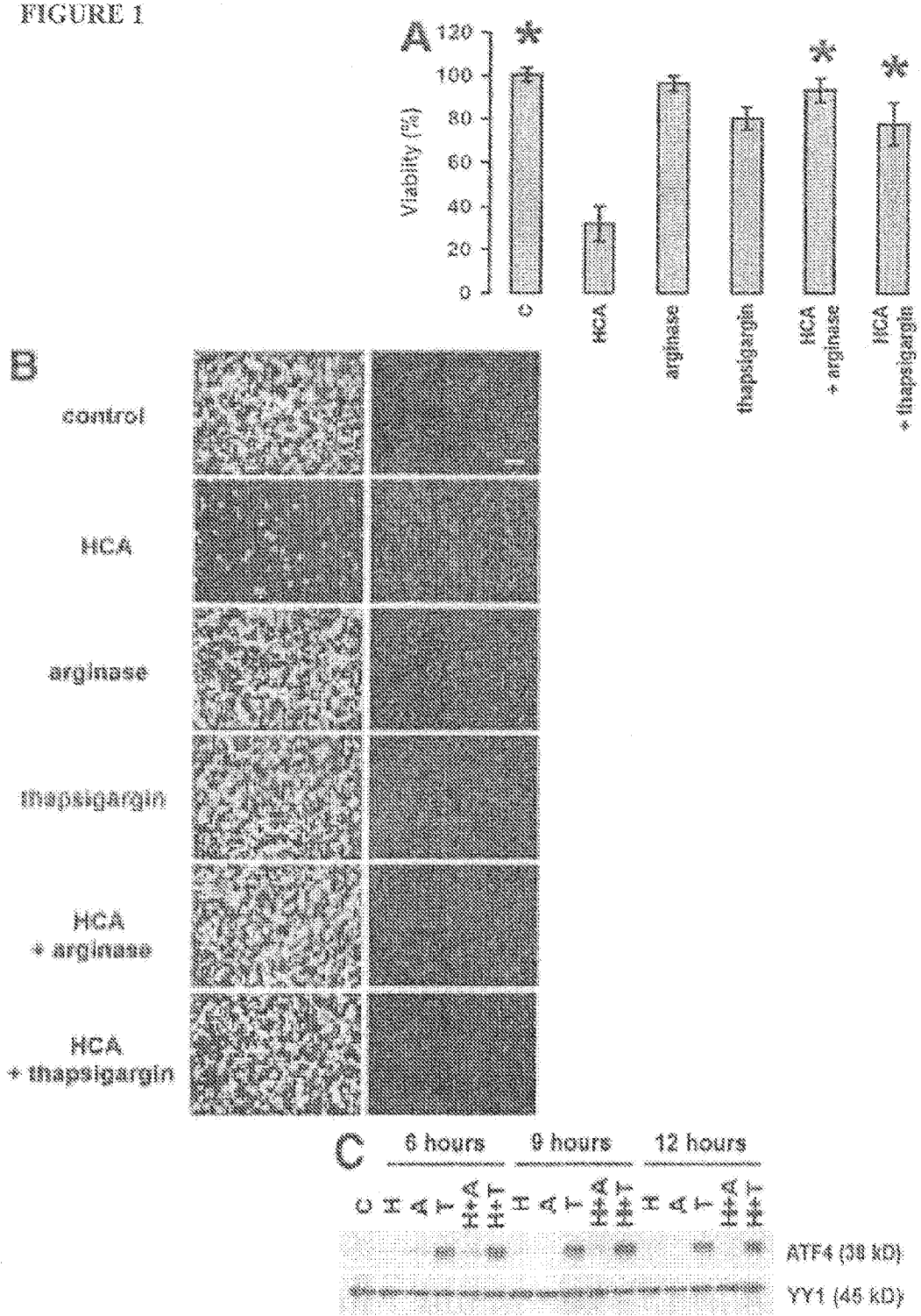
FIG. 1. Amino acid depletion and thapsigargin treatment induce ATF4 and protect embryonic cortical neurons from oxidative stress-induced cell death. (A) Cortical neuronal cultures (1 d in vitro) were treated with a vehicle control (shown as C), 10 mM of the glutamate analogue HCA, 1 µg/ml arginase, 1 µM thapsigargin, 1 µg/ml arginase and 10 mM HCA, or 10 mM HCA and 1 µM thapsigargin. 24 h later, cell viability was determined using the MTT assay. The graph depicts mean (compared with control)±SD calculated from three separate experiments for each group (n=25). *, P<0.05 from HCA-treated cultures by the Kruskal-Wallis test followed by Dunn's multiple comparisons test. (B) Live/dead assay of cortical neuronal cultures (2 d in vitro). Live cells were detected by uptake and trapping of calcein-AM (green fluorescence). Dead cells failed to trap calcein but were freely permeable to the highly charged DNA intercalating dye ethidium homodimer (red fluorescence). Bar, 50 µm. (C) Treatment with 10 mM HCA (shown as H) and 1 µg/ml arginase (shown as A) or 1 µM thapsigargin (shown as T), alone or in combination with HCA, increases the expression of ATF4 in cultured cortical neurons as compared with vehicle-treated control (shown as C). Cells were harvested at the indicated time points, and nuclear extracts were separated using gel electrophoresis and immunodetected using an antibody against ATF4. YY1 was monitored as a loading control. The immunoblot is a representative example of three experiments.

The invention is based on the surprising discovery by the inventor that ATF4 protein (i.e., activating transcription factor 4) increases the likelihood of neural cell death from oxidative stress. The inventors further discovered that a reduction of ATF4 activity renders neurons resistant to neural cell death. Specifically, a reduction in ATF4 activity in mammals was shown to protect the mammalian brain from stroke-induced injury and disability. A reduction of ATF4 activity caused the mammals to recover more easily and maintained proper motor function more efficiently following stroke-induced injury and disability.

Method for Identifying a Drug Candidate

In one aspect, the invention relates to a method for identifying a drug candidate with activity as a neuroprotective agent. The method includes determining whether a compound reduces ATF4 activity, and identifying the compound that reduces ATF4 activity as a drug candidate.

The term "drug candidate" refers to any compound that has a putative or possible effect as a neuroprotective agent in a mammal. Examples of compounds include biological molecules and small molecules.

A biological molecule is any molecule which contains a more than one nucleotide, saccharide, or a amino acid unit, and has a molecular weight greater than about 450. Molecules that contain more than one nucleotide units include nucleic acids, oligonucleotides and polynucleotides. Molecules that contain more than one saccharide unit include disaccharides, trisaccharides, oligosaccharides (more than four saccharides) and polysaccharides. Molecules that contain more than one amino acid units include oligopeptides, peptides, proteins, and polypeptides.

Biological molecules further include derivatives of any of the molecules described above. For example, derivatives of biological molecules include lipid and glycosylation derivatives of molecules that contain more than one. amino acid unit, e.g., lipoproteins and glycoproteins. Derivatives of biological molecules further include lipid and glycosylated derivatives of molecules that contain more than one, saccharide unit, e.g. lipopolysaccharides and glycopolysaccharides. Derivatives of biological molecules further include proteo derivatives of molecules that contain more than one nucleotide units.

Small molecules are typically organic compounds, including organometallic and organosilicon compounds, and the like, and generally have molecular weights of approximately 450 or less. Small molecules can further include molecules that would otherwise be considered biological molecules, except their molecular weight is not greater than approximately 450. Thus, small molecules can include monosaccharides, oligosaccharides, amino acids, oligopeptides, nucleotides, oligonucleotides, and their derivatives, having a molecular weight of approximately 450 or less.

It is emphasized that a small molecule can have any molecular weight. They are merely called small molecules because they do not qualify as biological molecules, and typically have molecular weights less than approximately 450.

A drug candidate with "activity" as a neuroprotective agent refers to an ability to induce a neuroprotective effect upon in vitro, ex vivo, or in vivo administration of the drug candidate. Neuroprotective effects include preventing or reducing the likelihood of one or more of the following events: an increase in cytoplasmic swelling of a neural cell, a decrease in the number of dendrites attached to a neuron, a decrease in the number of synapses associated with a neuron, a decrease in the branching of dendrites, and a decrease in nucleus integrity in a neural cell.

The term "neuroprotective agent" refers to a substance, e.g., a compound, cell, etc., that limits neural dysfunction and/or death in the central nervous system (CNS) and peripheral nervous system (PNS) by inducing neuroprotective effects. Neuroprotective effects include maintaining neuronal viability, which includes maintaining integrity of normal cellular interactions and normal neural function. The neural dysfunction and/or death may result from acute disorders (e.g., stroke, CNS, or PNS injury or trauma) or from the onset of a neurodegerative disease or condition (e.g., Parkinson's, Alheimer's, Multiple Sclerosis).

A compound is identified as a drug candidate with activity as a neuroprotective agent by determining whether the compound reduces the activity of (activating transcription factor 4) ATF4, which is also referred to as CREB2. ATF4 is a stress response transcription factor that is expressed constitutively only at low concentrations, but gets rapidly induced under particular cell stress conditions. Once translated, ATF4 protein binds to the promoter regions of an array of different target genes including many that are involved in amino acid metabolism and redox control.

As used herein, "ATF4" refers to human ATF4 having a nucleic acid sequence and amino acid sequence as set forth in GenBank accession numbers NM_182810, NM_001675, and CU012942. The term "ATF4" further includes a nucleic acid and amino acid sequence having at least 95 percent homology (i.e., identity) to the sequences set forth in GenBank, as determined by methods known in the art.

A compound that "reduces" ATF4 activity refers to a compound that decreases a measurable level of ATF4 activity in a given assay in the presence of the compound, relative to a measurable level of ATF4 activity in the absence of the compound when tested under the same conditions.

Activity is considered reduced according to the invention if it is reduced at least about 10%, preferably, at least about 20%, more preferably at least about 30%, even more preferably at least about 40%, and most preferably at least about 50% or more than in the absence of the compound. Optimally, at least about 70%, more optimally at least about 85%, and most optimally 100% of the ATF4 activity in a cell is reduced in a neural cell.

"ATF4 activity" as used herein can be reduced by any mechanism. For example, ATF4 activity could be reduced by a reducing transcriptional induction of its cognate messenger RNA (mRNA), decreasing stability of ATF4 mRNA, decreasing translation of ATF4 mRNA into protein, decreasing stability of ATF4 protein, decreasing ATF4 activity (in the presence or absence of decreased protein), inhibiting binding of ATF4 to its target DNA, or any other mechanism.

In one embodiment, the act of determining whether a compound reduces ATF4 activity includes providing a cell expressing ATF4, contacting the cell with the compound, and measuring the level of ATF4 activity in the cell, wherein a decrease in the level of ATF4 activity in the cell in the presence of the compound indicates that the compound is able to reduce ATF4 activity.

The act of determining whether a compound reduces ATF4 activity in a given cell may also be determined indirectly by determining either the amount of ATF4 mRNA or the amount of ATF4 protein produced by the cell before and after contact with the compound. The level of mRNA transcribed from the ATF4 gene or the level of ATF4 protein encoded by the ATF4 gene in the cell may be determined by quantitative methods known in the art.

Any cell that expresses ATF4 may be used in the method of the invention. Expression may occur in the cell in vitro or in vivo.

Examples of a suitable cell that expresses ATF4 in vitro include a neural cell and a cell from the mouse hippocampal cell line HT22-ATF4-Puro, and several cancer cell lines as disclosed in Fels, et al. 2006, *Cancer Biol. Ther.* 5:723-728; Shringarpure, et al. 2006, *Br. J. Haematol.* 134:145-156; Torigoe, et al. 2005, *Curr. Med. Chem. Anticancer Agents.* 5:15-27; Park, et al. 2004, *J. Natl. Cancer Inst.* 96:1300-1310; Tanabe, et al., 2003, *Cancer Res.* 63:8592-8595. The cell may be derived from any mammal, such as a mouse, rat, or human. Preferably, the cell is derived from a human.

Cells that express ATF4 in vitro may require a known compound to induce ATF4 expression, such as thapsigargin and tunicamycin. Accordingly, in one embodiment, the level of ATF4 activity in the cell in the presence of the test compound is measured in relation to a level of ATF4 activity in the cell contacted with thapsigargin or tunicamycin.

Examples of a suitable cell that expresses ATF in vivo include neural cells. Any neural cell may be involved in the methods of the invention. As used herein, a "neural cell" includes nerve cells (i.e., neurons, e.g., uni-, bi-, or mulipolar neurons) and their precursors and glial cells (e.g., macroglia such as astrocytes, oligodendrocytes, ependymal cells, radial glia, Schwann cells, Satellite cells, and microglia) and their precursors. Microglia are specialized macrophages capable of phagocytosis that protect neurons of the central nervous system. The term "precursor" refers to cells which are capable of developing into a specific cell type. For example, a neural cell precursor is a cell which is capable of developing into a mature neural cell (i.e., a cell having the characteristic morphology and function of a neural cell).

Examples of cells that may undergo neural cell injury or death include cells of the central nervous system (CNS) or peripheral nervous system (PNS), including neurons, ganglia, Schwann cells, astrocytes, oligodendrocytes, microglia cells, endothelial cells, immune cells (e.g., macrophages, T cells, B cells, and neutrophils), etc.

Suitable cells include those of mammals, e.g., laboratory animals, such as mice, rats, and other rodents; monkeys, baboons, and other primates, etc. In one embodiment, the cell is a human cell.

The act of determining whether a compound reduces ATF4 activity includes contacting the cell expressing ATF4 with the compound. The term "contacting" refers to directly or indirectly bringing the cell and the compound together in physical proximity. The contacting may be performed in vitro or in vivo. For example, the cell may be contacted with the compound by delivering the compound into the cell through known techniques, such as microinjection, injecting the compound into the bloodstream of a mammal, and incubating the cell in a medium that includes the compound.

Incorporation of Sequence Listing

Incorporated herein by reference in its entirety is the Sequence Listing for the application. The Sequence Listing is disclosed on a computer-readable ASCII text file titled, "sequence listing.txt", created on Feb. 3, 2010. The sequence listing.txt file is 4 kb in size.

The act of determining whether a compound reduces ATF4 activity further includes measuring the level of ATF4 activity in the cell. The level of ATF4 may be measured by any method known in the art, including for example, PCR analysis, RT-PCR, Northern blot, Western blot, immunohistochemistry, ELISA assays, luciferase reporter assays, etc. For example, the level of ATF4 activity may be assessed by measuring the level of induction of a reporter gene (e.g., luciferase) that is operably linked to the ATF4 gene.

The level of ATF4 activity may also be assessed by detecting the level of activity of a gene that is targeted by ATF4. Genes that are targeted by ATF4 include, for example, heme oxygenase 1, stanniocalcin2, osteocalcin, gadd153/CHOP, and TRB3. Typically, the level of ATF4 activity in a given cell is measured in the presence of and in the absence of the test compound.

Identifying drug candidates typically involves multiple phases. During the early stages, compounds, preferably large libraries of compounds are screened or tested in vitro for binding to and/or biological activity at ATF4.

The compounds that exhibit activity ("active compounds" or "hits") from this initial screening process are then tested through a series of other in vitro and in vivo tests to further characterize the neuroprotective activity of the compounds.

The in vivo tests at this phase may include tests in non-human mammals such as those mentioned above. If a compound meets the standards for continued development as a drug following in vitro and in vivo tests, the compound is typically selected for testing in humans.

A progressively smaller number of test compounds at each stage are selected for testing in the next stage. The series of tests eventually leads to one or a few drug candidates being selected to proceed to testing in human clinical trials. The human clinical trials may include studies in a human suffering from a medical condition that can be treated or prevented by reducing ATF4 activity.

Suitable drug candidates for the methods described herein are preferably, but not necessarily, approved by a governmental entity responsible for approving drugs for human use (e.g., the United States Food and Drug Administration, and comparable national and regional agencies outside the United States).

Method for Reducing ATF4 Activity in a Neural Cell

In another aspect, the invention relates to a method for reducing ATF4 activity in a neural cell in a human in need thereof. The method includes administering to the human an effective amount of: Thimerosal; Gambogic Acid; Anthothecol; Disulfuram; Pyrithione Zinc; Thiram; Tomatine; Dihydrogambogic Acid; Trifluoperazine Hydrochloride; Alexidine Hydrochloride; Phenylmercuric Acetate; Pristimerin; Aklavine Hydrochloride; 6,3'-Dimethoxyflavone; Tetrachloroisophthalonitrile; Actinomycin D; Cedrelone; Pyrromycin; Mitoxanthrone Hydrochloride; Tyrothricin; Selinidin; Gentian Violet; Clofoctol; Aminacrine; Penicillic Acid; Byssochlamic Acid; Hieracin; Atranorin; Dihydrojasmonic Acid; Deltaline; Azaserine; Sodium Fluoroacetate; Thalidomide; Neomycin Sulfate; Camptothecin; Trimedlure (5-Cl Isomer Present); Chlorguanide Hydrochloride; Benzo[a]pyrene; Hycanthone; Methotrexate; Dihydrorotenone; Galanthamine Hydrobromide; Ipraflavone; 5,7-Dichlorokynurenic Acid; Haematoporphyrin Dihydrochloride; Osthol; 1r,2s-Phenylpropylamine; 2,4-Dinitrophenol; Bromopride; Isorotenone; Lycorine; Halcinonide; 7-Desacetoxy-6,7-Dehydrogedunin; 6-Aminonicotinamide; 6alpha-methylprednisolone acetate; Teniposide; 1-Methylxanthine; Mercaptopurine; Tripelennamine Citrate; 9-Amino-1,2,3,4-Tetrahydroacridine Hydrochloride; Beta-Dihydrorotenone; Acivicin; Hydroxytacrine Maleate; or Cetylpyridinium Chloride. See FIG. 12. Such compounds reduce ATF4 activity in vitro, ex vivo, or in vivo.

A human in need of a method for reducing ATF4 activity in a neural cell include a human suffering from a memory deficit; a memory surfeit; a stroke; ischemia; trauma to the central nervous system or peripheral nervous system; epilepsy-related brain damage, poisoning with a neurotoxic compound, or radiation-induced brain damage; an infectious disease of the central nervous system or peripheral nervous system; a cancer of the central nervous system or peripheral nervous system; and a neurodegenerative disease or condition.

The method for reducing ATF4 is especially useful in a human suffering from a neurodegenerative disease or condition. A neurodegenerative disease or condition includes Alexander disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, Huntington disease, HIV-associated dementia, Kennedy's disease, Krabbe disease, Lewy body dementia, Machado-Joseph disease (Spinocerebellar ataxia type 3), Multiple sclerosis, Multiple System Atrophy, Neuroborreliosis, Parkinson disease, Pelizaeus-Merzbacher Disease, Pick's disease, Primary lateral sclerosis, Prion diseases, Refsum's disease, Sandhoff disease, Schilder's disease, Schizophrenia, Spielmeyer-Vogt-Sjogren-Batten disease (also known as Batten disease), Spinocerebellar ataxia (multiple types with varying characteristics), Spinal muscular atrophy, Steele-Richardson-Olszewski disease, Tabes dorsalis, depression or a psychiatric disorder in which elements of cognition and memory have become disordered.

Specifically, the method for reducing ATF4 is especially useful in a human suffering from dementia, which is a neurodegenerative disease or condition. More specifically, the dementia is age-related dementia, dementia related to vitamin deficiency, or alcohol-related dementia.

A human in need of a method for reducing ATF4 activity in a neural cell may also be a human in need of any of the methods described herein as comprising administering to the human an effective amount of a compound that reduces ATF4 activity. Such methods include, for example, protecting neural cells from neural cell injury or death; promoting recovery of neural cell function; promoting synaptic plasticity; and limiting oxidative stress.

In one embodiment, the method for reducing ATF4 activity by administering a compound that reduces ATF4 activity further includes prescribing or treating the human with physical therapy, psychotherapy, or a combination thereof.

Physical therapy includes treating disease, injury, or disability by physical and mechanical means (such as by massage, regulated exercise, water, light, heat, and electricity). Physical therapy may include robotic techniques, such as those described in Volpe B T et al (2005) Robotics and Other Devices in the Treatment of Patients Recovering from Stroke. Current Neurology and Neuroscience Reports 5:465-470.

Conditions that can be treated with a combination of reducing ATF4 activity and physical therapy include: muscular control, sport-related injuries, traumatic brain injury, stress incontinence, neurological conditions, such as stroke and multiple sclerosis, rehabilitation following amputation, and cardiopulmonary rehabilitation.

Psychotherapy refers to treating a mental or emotional disorder or related physical conditions by psychological means. Psychotherapy includes various therapy models used by clinical psychologists. Four major psychotherapy perspectives include psychodynamic, cognitive behavioral, existential-humanistic, and systems or family therapy. All psychotherapy models involve a formal relationship between the clinical psychologist and client. The client may be an individual, couple, family, or small group. Psychotherapies typically employ a set of procedures to form a therapeutic alliance, explore the nature of psychological problems, and encourage new ways of thinking, feeling, or behaving.

Conditions that can be treated with a method for reducing ATF4 activity and psychotherapy include: Anxiety Disorders such as those listed in the DSM-IV, including Generalized Anxiety Disorder, Panic Disorder (with and without Agoraphobia), Agoraphobia Without History of Panic Disorder, Specific Phobia, Social Phobia, Obsessive-Compulsive Disorder, Posttraumatic Stress Disorder, Acute Stress Disorder, and Anxiety Disorders.

Method for Protecting Neural Cells from Further Neural Cell Injury or Death

In another aspect, the invention relates to a method for protecting a neural cell from further neural cell injury or death in a human who has suffered neural cell injury or death. The method includes administering to the human an effective amount of a compound that reduces ATF4 activity.

"Protecting a neural cell from further neural cell injury or death" refers to decreasing the likelihood of further neural cell injury or death in a neural cell, as compared to the likelihood in the absence of a compound that reduces ATF4 activity. Protecting a neural cell includes being able to produce neuroprotective effects, as described above.

A human who has suffered a neural cell injury or death caused by a disease or disorder of the CNS or PNS may be susceptible to further neural cell injury or death. For example, a human who has suffered a first neural cell injury or death due to stroke are typically more susceptible or have a greater likelihood of suffering additional neural cell injury or death after the first episode of stroke. The increase in susceptibility is in relation to a human who have not suffered a first neural cell injury or death.

Method for Promoting Recovery of Neural Cell Function

In a further aspect, the invention relates to a method for promoting recovery of neural cell function in a human that has suffered neural cell injury or death. The method includes administering to the human an effective amount of a compound that reduces ATF4 activity.

"Promoting" recovery of neural cell function refers to increasing the likelihood of recovery of neural cell function following a neural cell injury or death. The neural cell injury or death may result in a partial or complete loss of an ability of the neural cell to properly function. The likelihood of recovery is in relation to the likelihood in the absence of a compound that reduces ATF4 activity.

"Recovery of neural cell function" refers to regaining at least in part the ability to perform a neural cell function properly, following a neural cell injury or death. Recovery can also refer to preservation of the ability of a neural cell to perform a function that it performed previous to a neural cell injury or death. The recovery of neural cell function may be due to partial or complete restoration of a structure of a neural cell that was subjected to a neural cell injury or death.

"Neural cell function" refers to any function, role, task, or activity performed by a normal neural cell. Neural cell functions include the ability to allow for processing and recalling of information; regulation of factors, hormones, proteins, or compounds relating to the CNS and PNS; stimulating release or uptake of endogenous chemicals; controlling of motor functions; receiving and processing sensory factors; maintaining consciousness, etc.

Method for Promoting Synaptic Plasticity

In yet a further aspect, the invention relates to a method for promoting synaptic plasticity in a human in need thereof. The method comprises administering to a human in need thereof an effective amount of a compound that reduces ATF4 activity.

"Promoting" synaptic plasticity refers to increasing the likelihood of synaptic plasticity in a neural cell following a neural cell injury of death. The likelihood of synaptic plasticity is in relation to the likelihood in the absence of a compound that reduces ATF4 activity.

"Synaptic plasticity" refers to the capacity of a neural cell to change its structure and/or function in response to a neural cell injury or death, environmental condition, experience, or ongoing CNS or PNS activity. Synaptic plasticity may involve the proliferation of neural cells, the growth or movement of neural cell processes and/or alterations in their shape. Synaptic plasticity may involve formation of new synaptic connections between or amongst neural cells, which may involve growth or movement of neural cells. Synaptic plasticity may further involve strengthening or weakening of existing synaptic connections.

A human in need of a method for promoting synaptic plasticity include a human in need of a method for reducing ATF4 activity in a neural cell, as described above.

Method for Limiting Oxidative Stress

In another aspect, the invention relates to a method for limiting oxidative stress in a human who has a condition in which oxidative stress is a mediator of injury. The method includes administering to the human an effective amount of a compound that reduces ATF4 activity.

"Limiting oxidative stress" refers to decreasing the likelihood of oxidative stress in relation to the likelihood in the absence of a compound that reduces ATF4 activity. "Oxidative stress" refers to a condition in which there is an overproduction of oxygen-free radicals or a deficiency in an antioxidant defense and repair mechanism, or both.

Disorders and Diseases

"Neural cell injury or death" refers to any physical alteration, disruption, physical or chemical insult to a neural cell, or disease or disorder in which reducing ATF4 activity is desired as described below. The neural cell injury or death may result in a partial or complete loss of an ability of the neural cell to properly function.

Disorders and diseases in which reducing ATF4 activity is desired for treatment include ischemia, neurodegenerative disease or condition, or stroke. Additional disorders and diseases in which reducing ATF4 activity is desired for treatment traumatic disorders (including but not limited to spinal cord injuries, spinal cord lesions, or other CNS pathway lesions), surgical nerve lesions, damage secondary to infarction, infection, exposure to toxic agents, malignancy, paraneoplastic syndromes, or patients with various types of neurodegenerative disorders of the central nervous system. A mammal suffering from neural cell injury or death includes a mammal that is suffering from a disease or disorder in which reducing ATF4 activity is desired.

Ischemia

Any mammal suffering from ischemia can be treated in accordance with the methods of the present invention. Ischemia generally refers to a condition of decreased blood flow to an organ, tissue and/or cell. The decrease in blood flow can be caused by, for example, constriction (e.g., hypoxemic vasoconstriction) or obstruction (e.g., clot, atherosclerotic plaque) of a blood vessel.

Ischemia can occur in any cell, organ, and/or tissue. Examples of cells, organs, and/or tissues which can be subjected to ischemia include neuronal cells (e.g., neurons, ganglia, Schwann cells, astrocytes, oligodendrocytes and microglia), brain, spinal cord, intestinal cells, kidney cells, heart and cardiac muscle cells such as myocytes, etc.

Neurodegenerative Disease or Condition

A neurodegenerative disease or condition typically refers to a disorder generally characterized by gradual and progressive loss of cells, tissue and/or organ of the central or peripheral nervous system. Examples of such cells, tissues and organs include, the brain, spinal cord, neurons, ganglia, Schwann cells, astrocytes, oligodendrocytes and microglia.

Any mammal suffering from any neurodegenerative disease or condition can be treated in accordance with the methods of the present invention. For example, the neurodegenerative disease or condition can be an acute condition. Acute conditions generally occur as a result of trauma to a cell, tissue and/or organ of the nervous system. The trauma can, for example, partially or completely block blood flow to the cell, tissue and/or organ. Examples of acute neurodegenerative conditions include head injury and brain injury.

Alternatively, the neurodegenerative disease or condition can be a chronic neurodegenerative condition. Examples of chronic neurodegenerative diseases and conditions include Parkinson's disease, Alzheimer's disease, Huntington's disease and Amyotrophic Lateral Sclerosis (also known as Lou Gherig's disease).

Additional examples of neurodegenerative disorders and diseases that can be treated by the invention include but are not limited to Alexander disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, Huntington disease, HIV-associated dementia, Kennedy's disease, Krabbe disease, Lewy body dementia, Machado-Joseph disease (Spinocerebellar ataxia type 3), Multiple sclerosis, Multiple System Atrophy, Neuroborreliosis, Parkinson disease, Pelizaeus-Merzbacher Disease, Pick's disease, Primary lateral sclerosis, Prion diseases, Refsum's disease, Sandhoff disease, Schilder's disease, Schizophrenia, Spielmeyer-Vogt-Sjogren-Batten disease (also known as Batten disease), Spinocerebellar ataxia (multiple types with varying characteristics), Spinal muscular atrophy, Steele-Richardson-Olszewski disease, Tabes dorsalis, and other dementias.

Stroke

Any mammal suffering from stroke can be treated in accordance with the methods of the present invention. Stroke is a type of cardiovascular disease that generally involves the interruption of blood flow to and/or within the brain. The interruption of blood flow can be due to, for example, a blockage or rupture of an artery or vessel. The blockage typically occurs from a blood clot. As a result of the interruption of blood flow, the brain does not receive sufficient amounts of blood.

Trauma of the CNS or PNS

Any type of trauma to the nervous system may be treated by the methods of the claimed invention. As described above, trauma of the CNS or PNS include, but are not limited to, spinal cord injuries, spinal cord lesions, other CNS pathway lesions, as well as injuries to the PNS, such as injuries to a nerve or neuron of the PNS and axon damage resulting in demyelination of the PNS. Such trauma can arise from either physical injury or disease. Any mammal suffering from a trauma of the CNS or PNS can be treated in accordance with the methods of the present invention.

For example, spinal cord injury refers to any damage to the spinal cord. The damage typically results in loss of function, such as mobility or feeling. Damage to the spinal cord can occur, for example, as a result or trauma (car accident, gunshot, falls, etc.) or disease (polio, spina bifida, Friedreich's Ataxia, etc).

Any injury to the spinal cord can be treated in accordance with the method of the present invention. For example, the injury can be a complete injury to the spinal cord. Complete injury typically refers to the lack of function (e.g., no sensation and no voluntary movement) below the site of injury. Both sides of the body are usually affected.

Alternatively, the injury may be an incomplete injury to the spinal cord. An incomplete injury generally refers to some function below the site of injury. For instance, a person with an incomplete injury may be able to move one limb more than another, may be able to feel parts of the body that cannot be moved, or may have more functioning on one side of the body than the other, etc.

Additional injuries, traumas, and insults include epilepsy related brain damage; infectious disease, such as bacterial or viral meningitis and meningo-encephalitis, or prion diseases; poisonings with neurotoxic compounds; and radiation-induced brain damage.

Dementia

Dementia is a loss of mental ability severe enough to interfere with normal activities of daily living, lasting more than six months, not present since birth, and not associated with a loss or alteration of consciousness.

Dementia is a group of symptoms caused by gradual death of brain cells. The loss of cognitive abilities that occurs with dementia leads to impairments in memory, reasoning, planning, and personality. While the over-whelming number of people with dementia are elderly, and can be a result of the process of aging. Dementia is also caused by specific brain diseases. Of these, Alzheimer's disease (AD) is the most common, followed by vascular or multi-infarct dementia.

Dementia is usually caused by degeneration in the cerebral cortex, the part of the brain responsible for thoughts, memories, actions and personality. Death of brain cells in this region leads to the cognitive impairment which characterizes dementia. This degeneration can be a result of the process of aging.

Another common cause of dementia is AD. The brain of a person with AD becomes clogged with two abnormal structures, called neurofibrillary tangles and senile plaques. Neurofibrillary tangles are twisted masses of protein fibers inside nerve cells, or neurons. Senile plaques are composed of parts of neurons surrounding a group of proteins called beta-amyloid deposits. Why these structures develop is unknown. Current research indicates possible roles for inflammation, blood flow restriction, and toxic molecular fragments known as free radicals. Several genes have been associated with higher incidences of AD, although the exact role of these genes is still unknown.

Vascular dementia occurs from decrease in blood flow to the brain, most commonly due to a series of small strokes (multi-infarct dementia). Other cerebrovascular causes include: vasculitis from syphilis, Lyme disease, or systemic lupus erythematosus; subdural hematoma; and subarachnoid hemorrhage. Because of the usually sudden nature of its cause, the symptoms of vascular dementia tend to begin more abruptly than those of aging or Alzheimer's dementia. Symptoms may progress stepwise with the occurrence of new strokes. Unlike AD, the incidence of vascular dementia is lower after age 75.

Other conditions which may cause dementia include: AIDS; Parkinson's disease; Lewy body disease; Pick's disease; Huntington's disease; Creutzfeldt-Jakob disease; brain tumor; hydrocephalus; head trauma; multiple sclerosis; prolonged abuse of alcohol or other drugs; vitamin deficiency: thiamin, niacin, or $B_{12}$; hypothyroidism; and hypercalcemia.

Compounds that Reduce ATF4 Activity

Any of the compounds listed above as being effective in the method for reducing ATF4 activity in a neural cell in a human in need thereof may be used in any of the methods described above as comprising administering to the human an effective amount of a compound that reduces ATF4 activity. Such methods include, for example, protecting neural cells from neural cell injury or death; promoting recovery of neural cell function; promoting synaptic plasticity; and limiting oxidative stress.

Similarly, the same compounds may be used in the disorders and diseases listed above as capable of being treated in accordance with the invention. These disorders and diseases include, for example, ischemia, any of the neurodegenerative diseases or conditions listed above, stroke, trauma of the CNS or PNS, and dementia.

A compound that reduces ATF4 activity or may be used in the disorders and diseases listed above as capable of being treated in accordance with the invention further includes compounds identified by the method for identifying a drug candidate with activity as a neuroprotective agent, as described above.

Administration

The compounds of the invention are administered to a human in an amount effective in achieving its purpose. The effective amount of the compound to be administered can be readily determined by those skilled in the art, for example, during pre-clinical trials and clinical trials, by methods familiar to physicians and clinicians. Typical daily doses include approximately 1 mg to 1000 mg.

Any method known to those in the art for contacting a cell, organ or tissue with a compound may be employed. Suitable methods include in vitro, ex vivo, or in vivo methods. In vitro methods typically include cultured samples. For example, a cell can be placed in a reservoir (e.g., tissue culture plate), and incubated with a compound under appropriate conditions suitable for reducing ATF4 activity. Suitable incubation conditions can be readily determined by those skilled in the art.

Ex vivo methods typically include cells, organs or tissues removed from a mammal, such as a human. The cells, organs or tissues can, for example, be incubated with the compound under appropriate conditions. The contacted cells, organs or tissues are normally returned to the donor, placed in a recipient, or stored for future use. Thus, the compound is generally in a pharmaceutically acceptable carrier.

In vivo methods are typically limited to the administration of a compound, such as those described above, to a mammal, preferably a human. The compounds useful in the methods of the present invention are administered to a mammal in an amount effective in reducing ATF4 activity or treating the mammal. The effective amount is determined during pre-clinical trials and clinical trials by methods familiar to physicians and clinicians.

An effective amount of a compound useful in the methods of the present invention, preferably in a pharmaceutical composition, may be administered to a mammal in need thereof by any of a number of well-known methods for administering pharmaceutical compounds. The compound may be administered systemically or locally.

For example, the compound may be administered orally, intravenously, intranasally, intramuscularly, subcutaneously, or transdermally. Other routes of administration include intracerebroventricularly or intrathecally. Intracerebroventiculatly refers to administration into the ventricular system of the brain. Intrathecally refers to administration into the space under the arachnoid membrane of the spinal cord. Thus intracerebroventricular or intrathecal administration may be preferred for those diseases and conditions which affect the organs or tissues of the central nervous system.

The compounds useful in the methods of the invention may also be administered to mammals by sustained release, as is known in the art. Sustained release administration is a method of drug delivery to achieve a certain level of the drug over a particular period of time. The level typically is measured by serum or plasma concentration.

A description of methods for delivering a compound by controlled release can be found in international PCT Application No. WO 02/083106. The PCT application is incorporated herein by reference in its entirety. Other controlled release agents are described, for example, in U.S. Pat. Nos. 5,567,439; 6,838,094; 6,863,902; and 6,905,708. The controlled release agents and methods for making them in these patents are incorporated herein by reference.

Any formulation known in the art of pharmacy is suitable for administration of the compounds useful in the methods of the present invention. For oral administration, liquid or solid formulations may be used. Some examples of formulations include tablets, capsules, such as gelatin capsules, pills, troches, elixirs, suspensions, syrups, wafers, chewing gum and the like. The compounds can be mixed with a suitable pharmaceutical carrier (vehicle) or excipient as understood by practitioners in the art. Examples of carriers and excipients include starch, milk, sugar, certain types of clay, gelatin, lactic acid, stearic acid or salts thereof, including magnesium or calcium stearate, talc, vegetable fats or oils, gums and glycols.

Formulations of the compounds useful in the methods of the present inventions may utilize conventional diluents, carriers, or excipients etc., such as those known in the art to deliver the compounds. For example, the formulations may comprise one or more of the following: a stabilizer, a surfactant, preferably a nonionic surfactant, and optionally a salt and/or a buffering agent. The compound may be delivered in the form of an aqueous solution, or in a lyophilized form.

The stabilizer may, for example, be an amino acid, such as for instance, glycine; or an oligosaccharide, such as for example, sucrose, tetralose, lactose or a dextran. Alternatively, the stabilizer may be a sugar alcohol, such as for instance, mannitol; or a combination thereof. Preferably the stabilizer or combination of stabilizers constitutes from about 0.1% to about 10% weight for weight of the compound. The surfactant is preferably a nonionic surfactant, such as a polysorbate. Some examples of suitable surfactants include Tween20, Tween80; a polyethylene glycol or a polyoxyethylene polyoxypropylene glycol, such as Pluronic F-68 at from about 0.001% (w/v) to about 10% (w/v).

The salt or buffering agent may be any salt or buffering agent. Some examples of salts include sodium or potassium chloride, or sodium or potassium phosphate. Preferably, the buffering agent maintains the pH of the pharmaceutical composition in the range of about 5.5 to about 7.5. Some examples of buffers include sodium or potassium biphosphate, sodium or potassium bicarbonate, and mixtures of carboxylic acids and salts thereof, such as, for example, ascetic acid/sodium acetate and citric acid/potassium citrate.

The salt and/or buffering agent is also useful to maintain the osmolality at a level suitable for administration to a human or an animal. Preferably the salt or buffering agent is present at a roughly isotonic concentration of about 150 mM to about 300 mM.

The formulations of the compounds useful in the methods of the present invention may additionally contain one or more conventional additive. Some examples of such additives include a solubilizer such as, for example, glycerol; an antioxidant such as for example, benzalkonium chloride (a mixture of quaternary ammonium compounds, known as "quats"), benzyl alcohol, chloretone or chlorobutanol; anaesthetic agent such as for example a morphine derivative; or an isotonic agent etc., such as described above. As a further precaution against oxidation or other spoilage, the pharmaceutical compositions may be stored under nitrogen gas in vials sealed with impermeable stoppers.

EXAMPLES

Example 1

Amino Acid Depletion and Thapsigargin Treatment Induce ATF4 and Protect Embryonic Cortical Neurons from Oxidative Stress-induced Cell Death Arginase and thapsigargin led to nearly complete protection from neuronal cell death (FIGS. 1, A and B) and to accumulation of ATF4 protein (FIG. 1 C). Interestingly, oxidative stress alone was shown to be was sufficient to induce ATF4 protein levels (FIG. 1 C).

Example 2

Cortical Neurons from ATF4$^{-/-}$ Brains are Resistant to Oxidative Stress-induced Cell Death To verify that the protection by arginase and thapsigargin requires ATF4, cortical neurons from brains of embryonic ATF4$^{-/-}$ mice (E 15.5) were cultured. Immunohistochemical analysis (FIG. 2 A) using an antibody to microtubule-associated protein 2 (MAP2; which stains neural dendrites) showed that basal viability and morphology of cell bodies and dendrites did not display any differences between ATF4$^{+/+}$ and ATF4$^{-/-}$ neurons. ATF4 mRNA was found to be induced in ATF4$^{+/+}$ neurons after oxidative stress and its absence in ATF4$^{-/-}$ neurons (FIG. 2 B) was confirmed.

Figure 2:
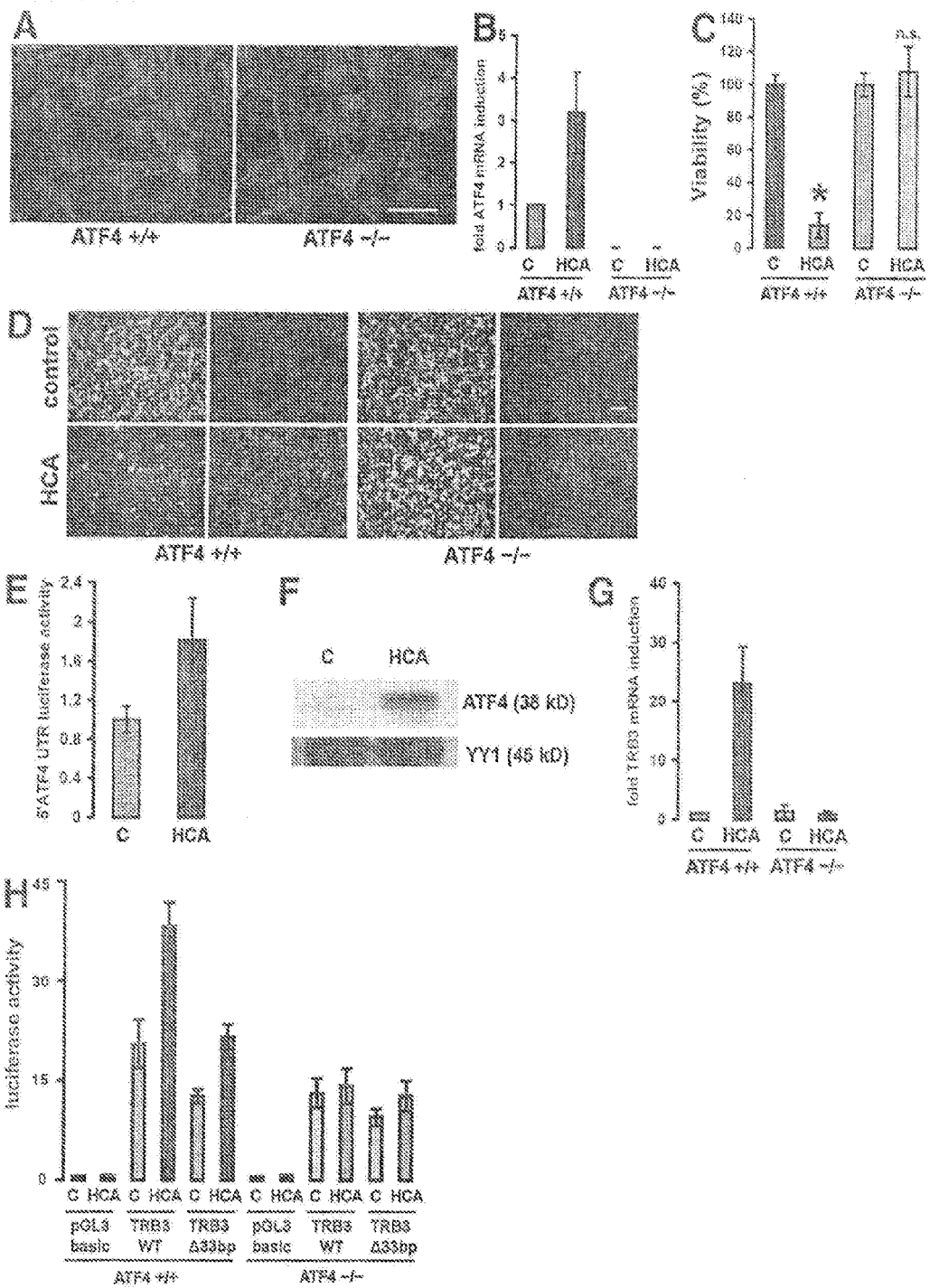
FIG. 2. Cortical neurons from ATF4$^{-/-}$ brains are resistant to oxidative stress-induced cell death. (A) Immunocytochemistry of cultured ATF4$^{+/+}$ and ATF4$^{-/-}$ cortical neurons. Cells were stained with an antibody against MAP2 (which stains neural dendrites; red) and counterstained with Hoechst (blue). Bar, 50 µm. (B) Real-time PCR of ATF4 mRNA expression in ATF4$^{+/+}$ and ATF4$^{-/-}$ neurons in response to treatment with 10 mM HCA. The value obtained from the ATF4$^{+/+}$ control was arbitrarily defined as 1. Mean±SD was calculated from three separate experiments. Each data point was performed in duplicate. (C) Cortical neuronal cultures (1 d in vitro) prepared from brains from ATF4$^{+/+}$ and ATF4$^{-/-}$ embryos were treated with a vehicle control (shown as C) or 10 mM HCA. 24 h later, cell viability was determined using the MTT assay. The graph depicts mean (compared with control)±SD calculated from data from five separate experiments (n=27 ATF4$^{+/+}$ and 73 ATF4$^{-/-}$). *, P<0.05 from ATF4$^{+/+}$ untreated cultures by the Kruskal-Wallis test followed by Dunn's multiple comparisons test. The difference between treated and untreated ATF4$^{-/-}$ neurons was not significant (n.s.). (D) Representative live/dead assay displaying untreated and HCA-treated ATF4$^{+/+}$ and ATF4$^{-/-}$ neurons. Bar, 50 µm. (E) ATF4$^{+/+}$ neurons were transfected with a reporter plasmid (pGL3 backbone) containing the mouse ATF4 5'UTR and AUG fused to luciferase. Cortical neurons were cotransfected with a plasmid expressing Renilla to allow normalization for transfection efficiency. 24 h after transfection, neurons were treated with vehicle control (shown as C) or 10 mM HCA. Cells were harvested in luciferase assay buffer 12 h after the onset of treatment. Values were calculated from three separate experiments and are given as the ratio of luciferase and Renilla activities (mean±SD; n=3). The value for treatment with vehicle control was arbitrarily defined as 1. (F) Oxidative stress results in nuclear accumulation of ATF4 in cultured cortical neurons. 60 µg of nuclear extracts from cortical neurons treated with 10 mM HCA or vehicle control (shown as C) were separated using gel electrophoresis and immunodetected using an antibody against ATF4. YY1 was monitored as a loading control. (G) Real-time PCR of TRB3 mRNA expression in ATF4$^{+/+}$ and ATF4$^{-/-}$ neurons in response to treatment with 10 mM HCA. The value obtained from the ATF4$^{+/+}$ control was arbitrarily defined as 1. Mean±SD was calculated from three separate experiments. Each data point was performed in duplicate. (H) ATF4$^{+/+}$ and ATF4$^{-/-}$ neurons were transfected with a luciferase reporter plasmid (pGL3 backbone) containing a 2-kb fragment of the mouse TRB3 promoter (TRB3WT), with a mutant version of this promoter lacking the 33-bp ATF4 binding site (TRB3Δ33 bp) or with the empty vector (pGL3 basic). Cortical neurons were cotransfected with a plasmid expressing Renilla to allow normalization for transfection efficiency. 24 h after transfection, neurons were treated with vehicle control (shown as C) or 10 mM HCA. Cells were harvested in luciferase assay buffer 12 h after the onset of treatment. Values are given as the ratio of luciferase and Renilla activities (mean±SD) and were calculated from three separate experiments. Each data point was performed in duplicate. Values are given as the ratio of luciferase and Renilla activities (mean±SD; n=3). The value for empty pGL3 was arbitrarily defined as 1.

Susceptibility to oxidative stress induced by the glutamate analogue homocysteate (HCA) in ATF4+/+ and ATF4$^{-/-}$ cortical neurons (FIGS. 2, C and D) was then examined. ATF4$^{-/-}$ neurons were found to be significantly protected from oxidative stress-induced death. ATF4$^{-/-}$ neurons demonstrated enhanced resistance, as monitored by MTT reduction (FIG. 2 C) and live/dead staining (FIG. 2 D). Moreover, in ATF4$^{+/+}$ neurons, ATF4 induction by treatment with HCA was a result of induction at the translational level (FIG. 2 E). The nuclear accumulation of ATF4 in ATF4$^{+/+}$ neurons exposed to oxidative stress (FIG. 2 F) was confirmed.

Higher nuclear ATF4 activity after oxidative stress was demonstrated by showing higher promoter activity of an ATF4 target gene, tribbles homologue 3 (TRB3), that has been recently associated with cell death. TRB3 mRNA is induced upon HCA treatment in an ATF4-dependent manner (FIG. 2 G).

To characterize ATF4 binding on the promoter of TRB3, a 2-kb fragment of the mouse TRB3 promoter (FIG. 2 H) was generated. This fragment contains a 33-bp element whose human analogue has been characterized as a DNA binding region of ATF4. Transfection of both ATF4$^{+/+}$ and ATF4$^{-/-}$ neurons with the TRB3WT promoter construct, along with a mutant version lacking the binding element, revealed that this element plays an important but not exclusive role in the induction of the TRB3 promoter after oxidative stress. In the absence of ATF4, the TRB3 promoter activity was not induced in response to oxidative stress.

Example 3

Microarray Analysis Reveals that ATF4 Regulates a Subset of Genes that are Induced in Response to Oxidative Stress To begin to examine whether ATF4 functions primarily as a repressor or activator in neurons and to determine the extent to which these ATF4-regulated genes function similarly in fibroblasts and neurons, a global analysis of gene expression using microarrays in ATF4 and ATF4$^{-/-}$ neurons (FIG. 3 A) was performed. More specifically, (a) the physiological genomic effect of ATF4 knockout (comparing ATF4$^{-/-}$ with ATF4$^{+/+}$ neurons), and (b) the effect of ATF4 knockout on the response to oxidative stress (comparing ATF4$^{-/-}$ with ATF4$^{+/+}$ neurons after HCA treatment; FIG. 3 B and FIG. 10) was assessed. At the chosen statistical threshold (5% false discovery rate), 136 probes were down-regulated in ATF4$^{-/-}$ versus ATF4$^{+/+}$ neurons, compared with 53 that were up-regulated, suggesting a role for ATF4 as a transcriptional activator. Functional gene ontology categories overrepresented in this list include mitochondrion, oxidoreductase activity, and amino acid metabolism.

Several of the down-regulated genes have been shown to be positively regulated by ATF4, including the prodeath gene TRB3. Comparison of ATF4$^{-/-}$ versus ATF4$^{+/+}$ neurons after oxidative stress with HCA treatment suggested a fundamental role of ATF4 in modulating oxidative stress-induced gene expression. In fact, 119 probes are dysregulated in response to oxidative stress in ATF4$^{+/+}$ neurons, whereas only 3 change in ATF4$^{-/-}$ neurons. Collectively, these findings suggest that ATF4 is a major upstream regulator of oxidative stress-induced changes in gene expression. Additionally, for most genes in embryonic cortical neurons, ATF4 functions as an activator and not a repressor.

FIG. 10 displays the differentially expressed genes in ATF4$^{-/-}$ neurons versus ATF4$^{+/+}$ neurons before and after HCA treatment. From each of the three contrasts, the top 30 genes with the highest fold change were selected. Ratios are log 2 transformed. Up-regulated genes (fold change>0.2) are highlighted in light grey, and down-regulated genes (fold change<−0.2) are highlighted in dark grey.

Gene expression array data were obtained from ATF4$^{-/-}$ fibroblasts that display a higher susceptibility to oxidative stress (Harding, et al., 2003, *Mol. Cell.* 11:619-633). A significant overlap could be observed between the array data from ATF4$^{-/-}$ fibroblasts and neurons (FIG. 11), indicating that ATF4 regulates at least a major part of target genes in a cell type-independent manner. These similarities do not explain the observation that ATF4 is prosurvival in fibroblasts and prodeath in neurons, but they demonstrate the reliability in the present analysis.

In contrast, a subset of genes, including the prodeath gene TRB3, were ATF4-regulated in neurons but not in fibroblasts. Collectively, these findings provide some understanding of the tissue-specific gene regulation mediated by ATF4 that could account for the divergent phenotypes in dividing fibroblasts versus postmitotic neurons.

FIG. 11 shows a comparison of the gene array data from this study with array data obtained from ATF4-deficient fibroblasts. An x indicates that the respective gene appears in both datasets as differentially expressed. 42 genes were extracted in the fibroblast array, of which 18 overlap with this study. These are 43% of the 42 genes of the fibroblast data resulting in a high level of significance at the hypergeometric test (P<0.00001).

Example 4

Figure 4:
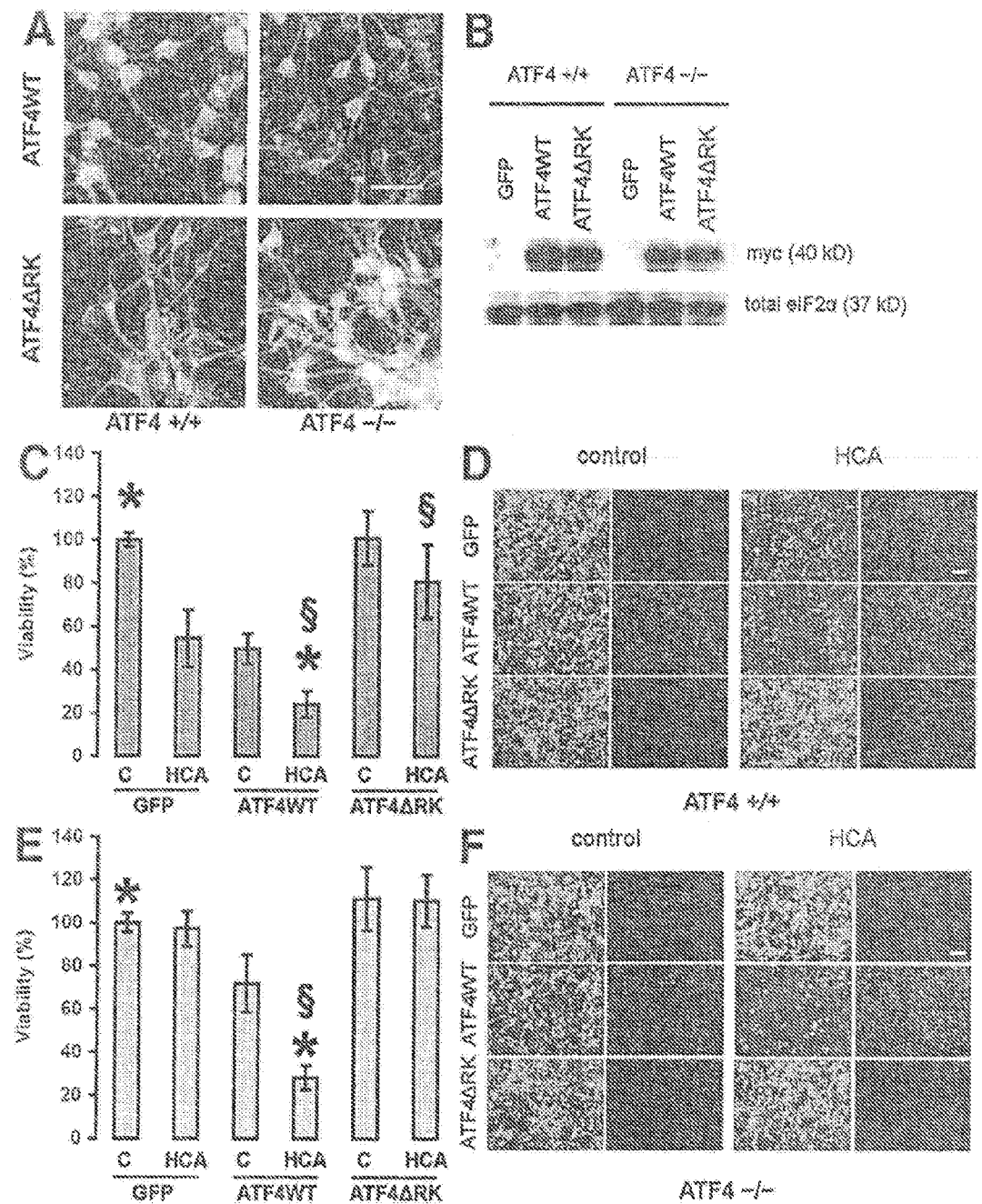
FIG. 4. Overexpression of ATF4WT restores sensitivity to oxidative stress and reduces neuronal viability itself. (A) Representative immunocytochemistry of ATF4$^{+/+}$ and ATF4$^{-/-}$ cortical neurons infected with the adenoviral constructs ATF4WT and ATF4ΔRK. Neurons were stained with antibodies against myc (green) and MAP2 (red), and were counterstained with Hoechst dye (blue). Bar, 50 µm (B) Whole-cell extracts obtained from both ATF4$^{+/+}$ and ATF4$^{-/-}$ neurons infected with GFP, ATF4WT, and ATF4ΔRK were separated using gel electrophoresis and immunodetected using an antibody directed against the myc tag. Total eIF2α was monitored as a loading control. (C) ATF4$^{+/+}$ cortical neurons were infected with GFP, ATF4WT, and ATF4ΔRK adenoviruses at an MOI of 100. 24 h after infection, neurons were treated with vehicle control (shown as C) or 10 mM HCA. 24 h later, cell viability was determined using the MTT assay. The graph depicts mean (compared with control)±SD calculated from four separate experiments for each group (n=45). P<0.05 by the Kruskal-Wallis test followed by Dunn's multiple comparisons test from untreated ATF4WT-overexpressing neurons (*) and from HCA-treated neurons overexpressing GFP (§). (D) Live/dead assay. Bar, 50 µm. (E) ATF4$^{-/-}$ cortical neurons were infected with GFP, ATF4WT, and ATF4ΔRK adenoviruses at an MOI of 100. 24 h after infection, neurons were treated with vehicle control (shown as C) or 10 mM HCA. 24 h later, cell viability was determined using the MTT assay. The graph depicts mean (compared with control)±SD calculated from four separate experiments for each group (n=28). P<0.05 by the Kruskal-Wallis test followed by Dunn's multiple comparisons test from untreated ATF4WT-overexpressing neurons (*) and from HCA-treated neurons overexpressing GFP (§). (F) Live/dead assay. Bar, 50 µm.

Overexpression of ATF4 is Sufficient to Restore Sensitivity to Glutathione Depletion-induced Cell Death and is Capable of Inducing Cell Death by Itself Because germline knockout animals (Masuoka, et al., 2002, *Blood.* 99:736-745) were used in this study, the possibility that the decreased susceptibility to oxidative stress was a consequence of a compensatory effect distantly related to ATF4 deficiency was analyzed. To address this possibility, adenoviral overexpression of a mouse ATF4WT construct was used. As a control, a dominant-negative ATF4 construct harboring a mutation in its DNA binding domain ($^{292}$RYRQKKR$^{298}$ to $^{292}$GYLEAAA$^{298}$) was use. To confirm the different DNA binding properties of these constructs, the 33-bp binding region of the TRB3 promoter by gel-shift (FIG. 4 A) and chromatin immunoprecipitation studies (FIG. 4 B)

was analyzed. In fact, only nuclear extracts from cells overexpressing ATF4WT in combination with WT oligonucleotide formed a band specific for ATF4. Consistently, only TRB3 promoter chromatin from cells overexpressing ATF4WT could be PCR amplified using primers flanking the ATF4 binding site. Cotransfection of WT and mutant ATF4 constructs with reporter constructs containing the WT and the mutant binding site confirmed the activating effect ATF4 has on transcription (FIG. 4 C).

Figure 5:
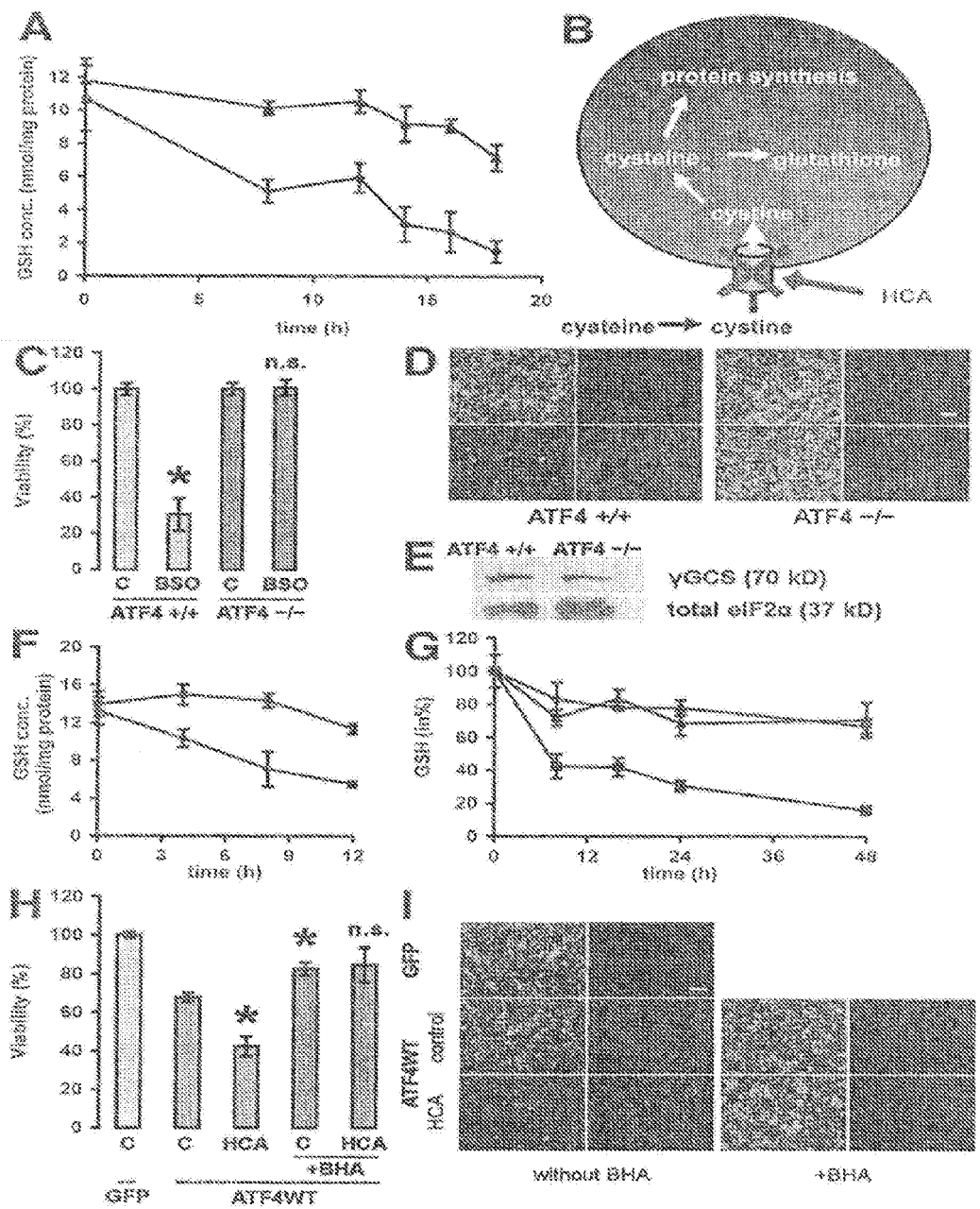
FIG. 5. ATF4 has a negative impact on the neuronal glutathione metabolism. (A) ATF4$^{+/+}$ (♦) and ATF4$^{-/-}$ (▲) cortical neurons were treated with 10 mM HCA. At the indicated time points, cells were trypsinized, washed, and pelleted. Reduced glutathione (GSH) was determined in the cell pellets using HPLC electrochemical detection. Data are from three separate cultures, and each data point was measured in duplicate. Graph depicts mean±SD. (B) Schematic overview over cysteine uptake and glutathione synthesis and their inhibition. (C) ATF4$^{+/+}$ and ATF4$^{-/-}$ cortical neurons were treated with a vehicle control (shown as C) or 200 µM BSO. 24 h later, cell viability was determined using the MTT assay. The graph depicts mean (compared with control)±SD calculated from five separate experiments for each group (n=46 ATF4$^{+/+}$ and 58 ATF4$^{-/-}$). *, P<0.05 from untreated ATF4$^{+/+}$ cultures by the Kruskal-Wallis test followed by Dunn's multiple comparisons test. The difference between treated and untreated ATF4$^{-/-}$ neurons was not significant (n.s.). (D) Live/dead assay displaying untreated and BSO-treated ATF4$^{+/+}$ and ATF4$^{-/-}$ neurons. Bar, 50 µm. (E) Protein expression of γ-GCS does not differ between ATF4$^{+/+}$ and ATF4$^{-/-}$ cortical neurons. Cytoplasmic extracts were separated using gel electrophoresis and immunodetected using an antibody against γGCS. Total eIF2α was monitored as a loading control. (F) ATF4$^{+/+}$ (♦) and ATF4$^{-/-}$ (■) cortical neurons were treated with 200 μM BSO. At the indicated time points, cells were trypsinized, washed, and pelleted. GSH was determined in the cell pellets using HPLC electrochemical detection. Data are from three separate cultures, and each data point was measured in duplicate. Graph depicts mean±SD. (G) ATF4$^{+/+}$ cortical neurons were infected with GFP (♦), ATF4WT (■), and ATF4ΔRK (▲) adenoviruses at an MOI of 100. At the indicated time points after infection, cells were trypsinized, washed, and pelleted. GSH was determined in the cell pellets using HPLC electrochemical detection. The graph depicts mean±SD calculated from three separate experiments for each group, and each data point was measured in duplicate. The value obtained from noninfected neurons was arbitrarily defined as 100%. (H) ATF4$^{+/+}$ cortical neurons were infected with GFP and ATF4WT adenoviruses at an MOI of 100. 24 h after infection, neurons were treated with vehicle control (shown as C), 10 mM HCA, 10 μM BHA, or a combination of both. The graph depicts mean (compared with control) ±SD calculated from five separate experiments for each group (n=29). *, P<0.05 from untreated neurons overexpressing ATF4WT by the Kruskal-Wallis test followed by Dunn's multiple comparisons test. The difference between neurons overexpressing ATF4WT treated with BHA alone and neurons overexpressing ATF4WT treated with both BHA and HCA was not significant (n.s.). (I) Live/dead assay. Bar, 50 μm.

To determine whether forced expression of ATF4 in ATF4$^{-/-}$ neuronal cultures can restore sensitivity to oxidative stress and/or has an effect itself, both constructs were overexpressed along with a GFP control in both ATF4$^{+/+}$ and ATF4$^{-/-}$ cortical neuronal cultures, followed by treatment with HCA (FIG. 5). The efficient expression of both ATF4 constructs in cortical neurons by immunohistochemistry (FIG. 5 A) and Western blotting (FIG. 5 B) was confirmed. Specifically, ~50% of neurons and a small number of glia are infected with the adenoviruses. Infection with ATF4ΔRK was able to protect ATF4$^{+/+}$ cortical neuronal cultures from HCA-induced toxicity (FIGS. 5, C and D), whereas infection with ATF4WT was capable of rendering ATF4$^{-/-}$ neurons sensitive to HCA (FIGS. 5, E and F).

Moreover, infection with ATF4WT itself significantly reduced the viability in both WT and ATF4$^{-/-}$ neurons. Combination of forced expression of ATF4WT and treatment with HCA resulted in a higher loss of viability than infection with ATF4WT alone, suggesting that at least one more pathway in addition to ATF4 is involved in HCA toxicity. Collectively, these results are consistent with the notion that ATF4 indeed plays a key role in oxidative stress-mediated cell death.

Example 5

ATF4 has a Negative Impact on Neuronal Glutathione Metabolism

The loss of glutathione is central to the in vitro model of oxidative stress used in this study. This model has been successfully used to describe signaling pathways that prevent cell death downstream of glutathione depletion. However, in fibroblasts, ATF4 has been described as a positive regulator of glutathione metabolism (Harding, et al., 2003, *Mol. Cell.* 11:619-633). Therefore, glutathione measurements were performed to determine whether ATF4 permits cell death in response to HCA by direct influence of the neuronal glutathione metabolism or by acting downstream of glutathione depletion.

Figure 6:
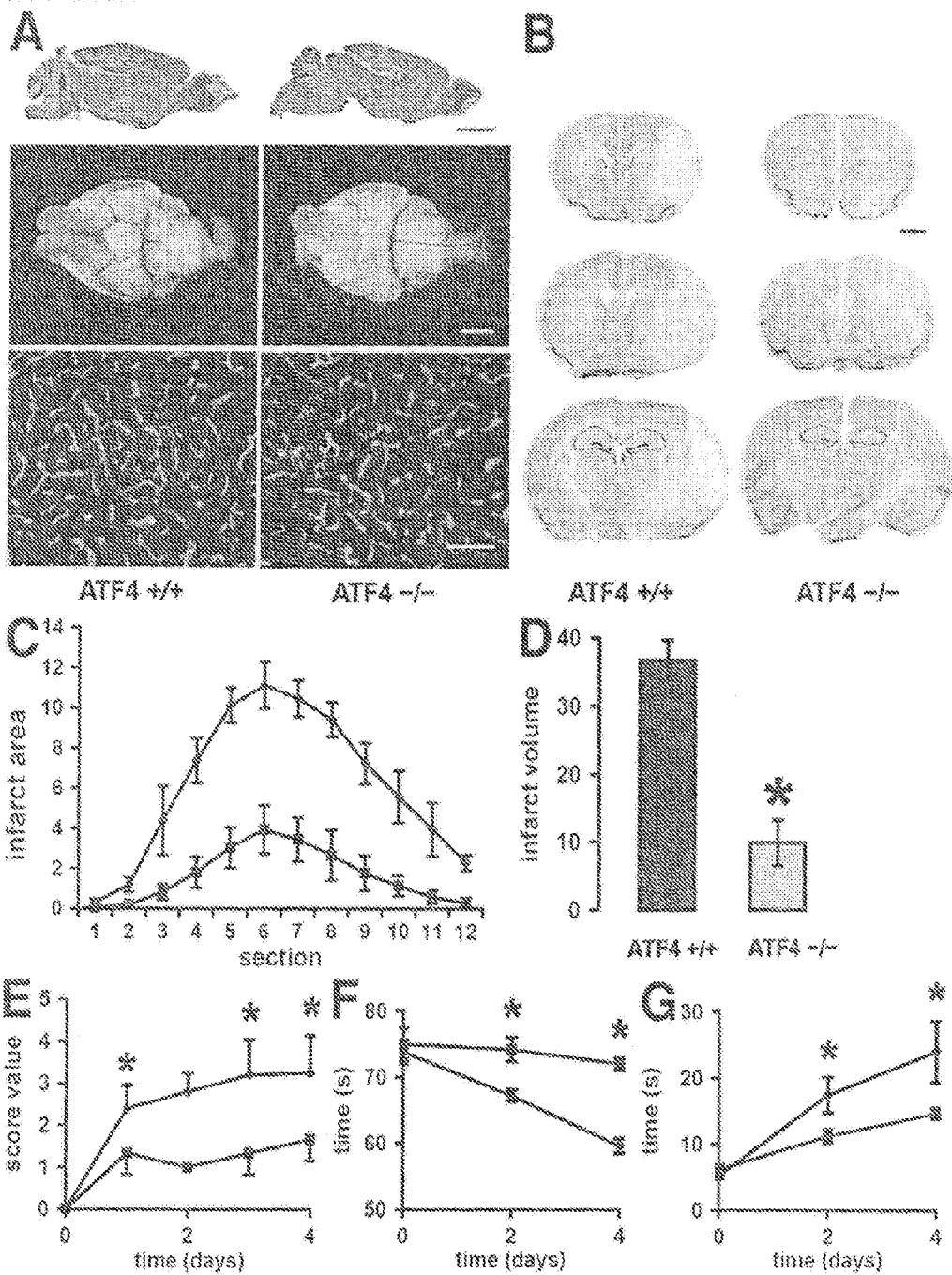
FIG. 6. Role of ATF4 in brain ischemia. (A, top) Sagittal sections of ATF4$^{+/+}$ (left) and ATF4$^{-/-}$ (right) brains stained with cresyl violet. Bar, 3,000 μm. (A, middle) Ventral view of large cerebral blood vessels of representative ATF4$^{+/+}$ (left) and ATF4$^{-/-}$ (right) mice that were perfused with India ink. Note the higher degree of tortuosity of the MCA in the brain from the ATF4$^{-/-}$ mouse. Bar, 3,000 μm. (A, bottom) Representative microscopic views of brain sections from ATF4$^{+/+}$ and ATF4$^{-/-}$ mice that were immunostained for the endothelial cell-specific marker CD31 (green). Bar, 100 μm. (B) Representative brain sections at 4 d after MCAo from ATF4$^{+/+}$ (n=5) and ATF4$^{-/-}$ (n=6) mice from rostral to caudal stained with cresyl violet to determine the infarct area. Bar, 1,000 μm. (C) The infarct area in ATF4$^{+/+}$ (♦) and ATF4$^{-/-}$ (■) brains was measured in 12 sequential sections taken from ATF4$^{+/+}$ (n=5) and ATF4$^{-/-}$ (n=6) mice at rostral to caudal regular intervals. Graph depicts mean±SD. (D) The infarct volume was assessed by adding the infarct volumes based on the infarct area in each section. Graph depicts mean±SD. *, P<0.0001 by the t test. (E) Scoring of neurological deficit was assessed at different time points of recovery in ATF4$^{+/+}$ (n=5) and ATF4$^{-/-}$ (n=4) mice. Graph depicts mean±SD. *, P<0.05 by the Mann-Whitney test. (F) Inclined plane test at different time points after stroke in ATF4$^{+/+}$ (n=5) and ATF4$^{-/-}$ (n=4) mice. The test measured the time a mouse managed to hold itself on an inclined glass plate angled at 50° before sliding down. Graph depicts mean±SD. *, P<0.05 by the t test. (G) Hanging wire test at different time points after stroke in ATF4$^{+/+}$ (n=5) and ATF4$^{-/-}$ (n=4) mice. The hanging wire test determined the time it took an animal to cross a distance of 45 cm on a freely hanging narrow metal bar. Graph depicts mean±SD. *, P<0.05 by the t test.

In untreated neurons, glutathione concentrations in ATF4$^{+/+}$ and ATF4$^{-/-}$ neurons did not differ (FIG. 6 A). HCA treatment caused a progressive loss of glutathione in ATF4$^{+/+}$ neurons. However, ATF4$^{-/-}$ neurons displayed a markedly slower decline in glutathione concentration.

To rule out the possibility that an increased rate of glutathione synthesis is responsible for decreased sensitivity to cystine deprivation-induced glutathione depletion (20), buthionine sulfoximine (BSO) was used to directly inhibit the rate-limiting enzyme of glutathione synthesis, γ-glutamyl-cysteine synthetase (γ-GCS; FIG. 6 B). BSO resulted in cell death in ATF4$^{+/+}$ neurons, whereas ATF4$^{-/-}$ neurons were essentially resistant (FIGS. 6, C and D). γ-GCS expression did not differ between ATF4$^{+/+}$ and ATF4$^{-/-}$ neurons at the protein level and did not appear in the gene array (FIG. 6 E). Similar to HCA, BSO treatment led to a decline in the concentration of glutathione in ATF4$^{+/+}$ neurons, whereas ATF4$^{-/-}$ neurons displayed a distinctly slower reduction of glutathione (FIG. 6 F). These findings are consistent with the notion that the differences in reduction of glutathione after HCA or BSO is not attributable to changes in synthesis.

To determine whether ATF4 directly regulates the neuronal glutathione content, glutathione in neurons with forced expression of ATF4WT, ATF4ΔRK, and GFP (FIG. 6 G) was measured. Consistent with the finding that forced expression of ATF4WT can reduce neuronal viability, this viability reduction was found to correlate with a reduction in the neuronal glutathione content. Because cell death attributable to glutathione depletion can be completely blocked by a whole host of classical antioxidants, the forced expression of ATF4WT was combined with butylated hydroxyanisol (BHA) treatment (FIGS. 6, H and I).

BHA is a well characterized antioxidant known to block HCA-induced cell death in cortical neurons (6). In fact, in neurons overexpressing ATF4WT, BHA significantly increased neuronal viability and protected against the additional toxic effect of HCA treatment. Finally, production of ROS was measured by using the redox-sensitive probe 2',7'-dichlorofluorescin (DCF; FIG. S1). ATF4$^{-/-}$ neurons displayed lower levels of ROS in response to HCA treatment than ATF4$^{+/+}$ neurons. These findings are consistent with the notion that ATF4 positively influences ROS levels and leads to a higher consumption of glutathione independent of its synthesis.

Example 6

ATF4$^{-/-}$ Animals are Less Susceptible to Ischemic Brain Damage

To test the hypothesis that ATF4 germline knockout animals have less neuronal loss after stroke, a transient middle cerebral artery occlusion (MCAo) model was used for ischemia-reperfusion injury, as previously described (Baranova, et al., 2007, *J. Neurosci.* 27:6320-6332).

First, morphological studies were performed to rule out that germline ATF4 deficiency causes a fundamental abnormality in the adult brain that would bias stroke outcome (Masuoka, et al., 2002, *Blood.* 99:736-745; Bagheri-Yarmand, et al., 2003, *J. Biol. Chem.* 278:17421-17429; Tanaka, et al., 1998, *Genes Cells.* 3:801-810; Hettmann, et al., 2000, *Dev. Biol.* 222:110-123).

Examining sagittal sections of brains from ATF4$^{+/+}$ and ATF4$^{-/-}$ animals (FIG. 7 A, top), did not detect any significant structural differences in the cerebellum, hippocampus, or cortex. The morphology of major cerebral blood vessels of the circle of Willis (FIG. 7 A, middle) (Baranova, et al., 2007, *J. Neurosci.* 27:6320-6332) were then assessed.

Besides a higher degree of tortuosity in the MCA, no major abnormalities were detected in the brains obtained from ATF4$^{-/-}$ mice. Finally, using immunofluorescent staining for the endothelial-specific marker CD31/PECAM, no significant differences in the density or morphology of the microvessels (FIG. 7 A, bottom) were observed. In addition, important physiological parameters did not differ between ATF4$^{+/+}$ and ATF4$^{-/-}$ animals (FIG. S2 and Table S2).

Figure 12A:
FIG. 12A. Chemical structure of Thimerosal.

FIG. 12 shows the physiological data from ATF4$^{+/+}$ and ATF4$^{-/-}$ mice. The data shown in FIG. 12 are the values for blood gases, pH, levels of bicarbonate, glucose, and lactate, and values for mean arterial blood pressure and body temperature. Measurements were carried out 45 min before and after MCAo for three animals each.

Figure 7:
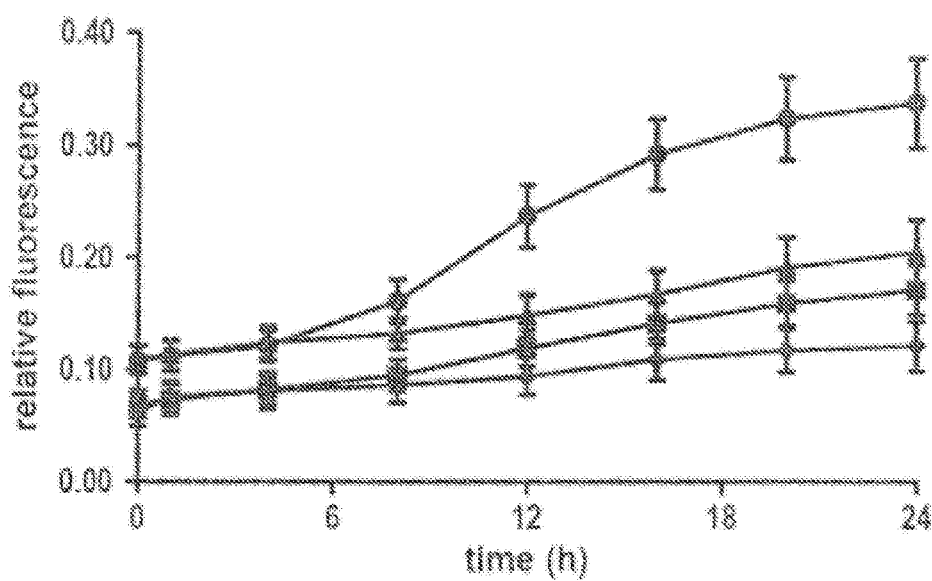
FIG. 7. ATF4$^{-/-}$ neurons display lower ROS levels in response to HCA treatment. ATF4$^{+/+}$ (Δ, untreated; ●, treated) and ATF4$^{-/-}$ (, untreated; ■, treated) cortical neurons were treated with 10 mM HCA. At the indicated time points, the cultures were incubated for 45 min with 1.25 μM DCF—$H_2$. Cells were washed with HBSS and read on a Fluorometer plate reader at 485-nm excitation and 530-nm emission wavelengths. Neurons that were not switched did not show any fluorescence and were used for background readings. Experiments were performed in three separate sets of cultures (ATF4$^{+/+}$, n=51; ATF4$^{-/-}$, n=21). Each data point was performed in duplicate. Values are mean±SD.

The procedure used to occlude the MCA (occlusion time=45 min) led to reproducible infarcts in WT animals involving both the cerebral cortex and the striatum, with sparing of the hippocampus. However, a significantly smaller infarct was observed when the procedure was performed in ATF4$^{-/-}$ animals (FIGS. 7, C and D). The smaller infarct area could be observed in all sections of the brain. Thus, the higher resistance to ischemia-reperfusion injury was not limited to a specific brain area. In fact, the smaller infarct volume was associated with a faster recovery in ATF4$^{-/-}$ animals, as measured by a simple neurological score (FIG. 7 E).

In addition, two simple behavioral tests (FIGS. 7, F and G) complemented the morphological data. In consideration of the eye lens malformation regularly observed in ATF4$^{-/-}$ animals (25), these tests are not dependent on the visual sense. Consistent with the morphological data, ATF4$^{-/-}$ animals performed significantly better than the ATF4$^{+/+}$ control group, suggesting that ATF4 deficiency facilitates recovery after stroke.

Example 7

ATF4 is a Prodeath Transcription Factor

These studies have led to the surprising conclusion that oxidants can trigger neuronal death via highly regulated signaling pathways and subsequent activation of prodeath transcription factors, leading to the controlled demise known as apoptosis. The current study adds to the present understanding of the cellular transcription factors that regulate neuronal viability and function after oxidative stress in primary cortical neurons.

Specifically, the transcription factor ATF4 was shown to be induced by oxidative stress caused by depletion of the major antioxidant tripeptide, glutathione. Transgenic deletion of ATF4 was demonstrated to render neurons resistant to neuronal cell death. Prevention of cell death by germline knockout of ATF4 is associated with a preservation of glutathione levels, the primary mediator of death in our oxidative stress model. Consistent with ATF4's role in regulating an early, upstream aspect of the oxidative neuronal death pathway, ATF4 deficiency was found to cause global down-regulation of gene expression and blocks the up-regulation of many genes that are induced by oxidative stress in WT neurons. Accordingly, forced expression of ATF4 was sufficient to promote cell death and loss of glutathione.

In addition, restoration of ATF4 protein expression was shown to reinstate sensitivity to oxidative death in ATF4$^{-/-}$ neurons. The relevance of protection by ATF4 deficiency was established by demonstrating that the ATF4 homozygous knockout is capable of protecting the adult mouse brain from stroke-induced injury and disability. ATF4$^{-/-}$ animals was shown to recover more easily and maintain proper motor function more efficiently. Although known to be a stress-responsive protein, these results for the first time establish ATF4 as a redox-regulated protein that can function to lower the threshold for oxidative stress-induced death in neurons.

Example 8

ATF4 is a Redox-regulated Transcription Factor

An up-regulation of ATF4 mRNA translational efficiency was observed after glutathione depletion. However, an increase in ATF4 mRNA levels was also observed after oxidative stress, thereby confirming a role for transcriptional regulation in ATF4 induction by cell stress. The distinct increase in ATF4 protein levels in the nucleus of neurons undergoing oxidative stress corresponded to an ATF4-dependent induction of a TRB3 promoter-luciferase reporter. Collectively, these observations show that oxidative stress-induced changes in ATF4 mRNA levels and translational efficiency lead to increased ATF4 activity in neurons.

Because ATF4 overexpression is sufficient to induce death, limiting the amount of ATF4, at least under basal conditions, is necessary for neuronal survival. Mechanisms that control and limit basal ATF4 activity appear to be important determinants of neuronal fate. Although this low level of ATF4 appears to be sufficient to regulate a host of genes, its absence does not grossly influence neuronal morphology or basal survival.

Example 9

ATF4 has a Direct Impact on Glutathione Metabolism

The above findings confirm the primary role that glutathione can play in neuronal death. The data presented in this study favor a model in which glutathione depletion causes an ATF4-dependent up-regulation of a coordinated set of genes that orchestrate the timely and irreversible demise of the cell. Part of the orchestrated sequence of events downstream of ATF4 activation includes the increased production of ROS and turnover of glutathione. Of note, many mitochondrial genes that could facilitate production of deleterious ROS during respiration are down-regulated in the ATF4$^{-/-}$ neurons.

Example 10

ATF4 Induces Global Transcriptional Changes

The above gene array data suggest that ATF4 acts at least in part as a transcriptional activator. This finding is in line a description of the activating effect of ATF4 on several target genes, such as heme oxygenase 1 (He, et al. 2001. *J. Biol. Chem.* 276:20858-20865; Alam, et al. 2003. *Curr. Pharm. Des.* 9:2499-2511), stanniocalcin 2 (Ito, et al. 2004. *Mol. Cell. Biol.* 24:9456-9469), osteocalcin (Yang, et al. 2004. *Cell.* 117:387-398), gadd153/CHOP (Averous, et al. 2004. *J. Biol. Chem.* 279:5288-5297), and TRB3 (Ohoka, et al. 2005. *EMBO J.* 24:1243-1255). Some of these target genes have been shown to play an important role in cell death and cell survival in the brain. Heme oxygenase 1 was demonstrated to be is induced in WT neurons by oxidative stress; however, it was down-regulated in ATF4–/– neurons. Likewise, stanniocalcin 2 is up-regulated in response to oxidative stress in WT neurons but was down-regulated in ATF4–/– neurons. A prodeath ATF4 target gene, TRB3, was strongly dependent on ATF4 and up-regulated in response to oxidative stress.

Example 11

The Prodeath Role of ATF4 Might be Context and Cell Type Specific

The data presented above show a prodeath role of ATF4. The finding that ATF4 activation can be associated with protection from oxidative stress-induced cell death, although it clearly acts as a prodeath transcription factor, points to a complex and context-specific role of ATF4 in the propagation of neuronal cell death. The gene expression data above indicates a highly significant overlap between data obtained from fibroblasts and from cortical neurons.

Example 12

ATF4 is a Prodeath Transcription Factor in vivo

ATF4 was established to play an important prodeath role in an in vivo model of stroke. No overt difference was observed when comparing the brain morphology between WT and ATF4$^{-/-}$ brains, including the vascular system. In addition, the smaller infarct size in the ATF4$^{-/-}$ mice could not be attributed to changes in systemic physiological parameters, including body temperature, or changes in cerebral blood flow under basal conditions or after MCAo. In summary, the strong correlation in the outcome between in vitro and in vivo studies lets us conclude that the above results provide an important role for ATF4 in the induction of neuronal cell death. Thus, ATF4 is an important target for therapeutic intervention against stroke and other neurodegenerative diseases.

Example 13

Materials and Methods

Animals.

All animal procedures were performed according to protocols approved by the Institutional Animal Care and Use Committee of the Weill Medical College of Cornell University. Germline ATF4$^{-/-}$ mice have been described previously (Masuoka, et al. 2002. *Blood.* 99:736-745). For the culture of mouse embryonic cortical neurons, embryos (15.5 days post conceptionem) were obtained from the mating of ATF4 heterozygous mice.

Primary Cortical Neurons and Cell Culture.

Primary neuronal cultures were prepared from the cerebral cortices of mouse embryos, as described previously (Siddiq, et al. 2005. *J. Biol. Chem.* 280:41732-41743), with minor modifications. The mouse hippocampal cell line HT22 was maintained according to standard procedures (Aminova, et al. 2005. *J. Biol. Chem.* 280:3996-4003). Transfection of both cortical neurons and HT22 cells was performed using Lipofectamine 2000 (Invitrogen) according to the manufacturer's instructions. Recombinant arginase was provided by D. Ash (Temple University, Philadelphia, Pa.).

Genotyping.

Genomic DNA for PCR was prepared using the DNeasy genomic DNA isolation kit (QIAGEN). The WT alleles were detected using the primer 5'-AGCAAAACAAGACAG-CAGCCACTA-3' (SEQ ID NO: 1). The ATF4$^{-/-}$ alleles (neomycin) were detected using the primer 5'-ATATTGCTGAA-GAGCTTGGCGGC-3' (SEQ ID NO: 2). As a common reverse primer, we used 5'-GTTTCTACAGCTTCCTCCTC-CACTCTT-3' (SEQ ID NO: 3).

Cell Viability/Cell Death Assays.

Cell viability was assessed by propidium iodide uptake and retention of calcein (Invitrogen) using an inverted epifluorescence microscope (Axiovert 200M; Carl Zeiss, Inc.). MTT assay was performed according to the manufacturer's instructions (Promega). In brief, absorbance was measured at 570 nm. From each data point, the reference absorbance measured at 690 nm was subtracted. Finally, values were calculated as the percentage of untreated control cells.

Plasmids.

The expression plasmids for ATF4WT and dominant-negative ATF4ΔRK (provided by J. Alam, Ochsner Foundation, New Orleans, La.) (He, et al. 2001. *J. Biol. Chem.* 276:20858-20865), and the mouse ATF4 5'UTR luciferase construct (D. Ron, New York University, New York, N.Y.) have been previously described. The promoter construct pTRB3 was generated by amplification of genomic mouse DNA using the primers 5'-CTCACTCAGGTGCCTGTAGTGCTCG-3' (SEQ ID NO: 4) and 5'-TCAGCAGAAGCAGCCAGAGGT-GTAG-3' (SEQ ID NO: 5), followed by a second round of PCR with the primers 5'-ACACTCGAGAGAGAAA-CAAATGTGTCATG-3' (SEQ ID NO: 6) and 5'-ACAAAGCTTCTAGAGAGCAAGGAAGAAAG-3' (SEQ ID NO: 7) before cloning into the vector pGL3basic (Promega). The mutant form lacking the 33-bp ATF4 binding site was generated using a site-directed mutagenesis kit (QuikChange; Stratagene). To generate the reporter plasmids with the 33-bp ATF4 binding sequence, the following oligonucleotides were annealed and cloned into pGL3 basic: p33WT, 5'-TCGAGGCAGATTAGCTCAGGTTTACAT-CAGCCGGGCGGGGATCCA-3' (SEQ ID NO: 8) and 5'-AGCTTGGATCCCCGCCCGGCTGATG-TAAACCTGAGCTAATCTGCC-3' (SEQ ID NO: 9); and p33MUT (mutant form), 5'-TCGAGGCAGATTAGCT-CAGTCTAAACCTATAGGGGCGGGGATCCA-3' (SEQ ID NO: 10) and 5'-AGCTTGGATCCCCGCCCCTATAGGTT-TAGACTGAGCTAATCTGCC-3' (SEQ ID NO: 11). All sequences were verified by automatic DNA sequencing.

Luciferase Assay.

Primary neurons and HT22 cells were transfected with the respective reporter construct along with the pTK-*Renilla* control (Promega). A dual luciferase assay (Promega) was performed using a bioluminometer (MDS Analytical Technologies), according to the manufacturer's instructions.

Adenoviruses.

To generate the adenoviruses ATF4WT and ATF4ΔRK, the expression cassettes of each construct were cloned into the shuttle vector ad5 pVQ-K-NpA. The correct sequence was confirmed by automatic DNA sequencing. Virus generation and amplification were performed by ViraQuest. Infection with adenoviruses was performed at a multiplicity of infection (MOI) of 100.

Gene Array Analysis.

RNA quantity was assessed with a spectrophotometer (Nanodrop; Thermo Fisher Scientific), and quality was assessed with nanochips (Bioanalyzer; Agilent Technologies). Total RNA was amplified, labeled, and hybridized on arrays (MouseRef-8 Expression BeadChip; Illumina). Data analysis was performed using Bioconductor packages (available at http://www.bioconductor.org; Gentleman, et al. 2004. *Genome Biol.* 5:R80). Raw data were log 2 transformed and normalized using quantile normalization. Analysis of differential expression was performed using a linear model fitting (LIMMA package; Smyth, G. K. 2005. Limma: linear models for microarray data. In Bioinformatics and Computational Biology Solutions Using R and Bioconductor. R. Gentleman, V. Carey, W. Huber, R. Irizarry, and S. Dudoit, editors. Springer, New York. 397-420). The obtained p-values were corrected for multiple testing using the false discovery rate method, and a threshold of 0.05 was applied. Microarray data have been deposited in the National Center for Biotechnology Information Gene Expression Omnibus under accession no. GSE10470.

DNA EMSA.

Crude nuclear extracts were purified by dialysis using Slide-A-Lyzer MINI Dialysis Units (Thermo Fisher Scientific). The following oligonucleotide probes (Invitrogen) corresponding to the ATF4 binding site of the TRB3 gene were used: TRB3WT, 5'-GATTAGCTCAGGTTTACATCAGC-CGGGCGGGGA-3' (SEQ ID NO: 12); and TRB3MUT, 5'-GATTAGCTCAGTCTAAACCTATAGGGGCGGGGA-3' (SEQ ID NO: 13). The oligonucleotides were annealed with complementary DNA and radiolabeled with γ-[$^{32}$P]ATP using T4 polynucleotide kinase. After incubation with nuclear extracts, the DNA-protein complexes were resolved in 5% polyacrylamide gels, and the signal was visualized using a PhosphorImager (Fujifilm).

Chromatin Immunoprecipitation Assay and PCR Amplification.

Formaldehyde cross-linking and chromatin immunoprecipitation were performed as described previously (Chavez, et al. 2006. *J. Neurosci.* 26:9471-9481). The cross-linked chromatin suspension was sonicated using a Sonicator 3000 (Mosonix). Immunoprecipitation was performed with an anti-myc antibody. DNA-protein cross-linking was reversed, followed by an overnight incubation at 65° C. DNA was isolated by phenol/chloroform extraction and subjected to PCR analysis using the primers 5'-GGTCACAGATGGTG-CAATCC-3' (SEQ ID NO: 14) and 5'-AACTGAG-CAGCTCTCGGAGTC-3' (SEQ ID NO: 15).

Glutathione Determination Using HPLC Electrochemical Detection and ROS Detection Using DCF Fluorescence.

Concentrations of reduced glutathione were measured using HPLC (PerkinElmer) equipped with an eight-channel coulometric array detector (ESA, Inc.). Cells were lysed in 5% (wt/vol) metaphosphoric acid and centrifuged at 10,000 g for 10 min to sediment protein. Cell-pellet precipitates were saved for protein determinations. Glutathione concentrations of supernatant fractions were determined by injecting 5-µl aliquots onto an Ultrasphere 5 u, 4.6×250 mm, C18 column (Beckman Coulter), and eluting with a mobile phase of 50 mM $NaH_2PO_4$, 0.05 mM octane sulfonic acid, 1.5% acetonitrile (pH 2.62) at a flow rate of 1 ml/min. Peak areas were analyzed using software from ESA, Inc. Intracellular generation of ROS was determined by DCF. Cortical neurons were seeded in 96-well fluorescence plates. After the treatments indicated in the figures, the cultures were incubated for 45 min with 1.25 µM $DCF-H_2$. Cells were washed with HBSS and read on a plate reader (Fluorometer; MDS Analytical Technologies) at 485-nm excitation and 530-nm emission wavelengths.

Cerebral Ischemia.

Transient focal cerebral ischemia was induced by MCAo using the intraluminal filament method, as previously described (Baranova, et al. 2007. *J. Neurosci.* 27:6320-6332). Male mice were anesthetized. A small incision was performed in the skin covering the scalp, and a fiber optic probe was glued to the parietal bone and connected to a laser-Doppler flowmeter (Periflux System 5010; Perimed) for continuous monitoring of cerebral blood flow. For MCAo, a heat-blunted black monofilament surgical suture (6-0) was inserted into the exposed external carotid artery, advanced into the internal carotid artery, and wedged into the circle of Willis to obstruct the origin of the MCA. The filament was left in place for 45 min and withdrawn.

Physiological Parameters.

Animal physiology was assessed in $ATF4^{+/+}$ and $ATF4^{-/-}$ mice (n=3 each). For this purpose, the left femoral artery was cannulated using a polyethylene tube (PE-10; BD Biosciences) to record mean arterial blood pressure. Blood samples were taken for chemical analysis using a hand-held blood analyzer (iSTAT; Abbot Laboratories).

Quantification of Infarct Volume.

Coronal brain sections were serially cut in a cryostat (Leica) and stained with cresyl violet to identify viable tissue. To correct for the effect of edema, the infarcted area was determined indirectly by subtracting the area of the healthy tissue in the ipsilateral hemisphere from the area of the contralateral hemisphere on each section. Infarction volume was calculated by integration of infarct areas measured in 20 equidistant brain sections that encompassed the whole lesion. Volumes from all sections were summed to calculate total infarct volume.

Cerebral Macrovascular Morphology.

To assess the morphology of major cerebral blood vessels of the circle of Willis, deeply anesthetized mice were perfused transcardially with a prewarm (37° C.) saline solution containing gelatin (20% wt/vol) and India ink (0.25% vol/vol).

Neurological Evaluation.

Neurological scores were assigned the following values: 0, normal motor function; 1, flexion of torso and contralateral forelimb when the mouse was lifted by the tail; 2, circling to the contralateral side when the mouse was held by the tail on a flat surface, but normal posture at rest; 3, leaning to the contralateral side at rest; and 4, no spontaneous motor activity. The inclined plane test measured the time a mouse managed to hold itself on an inclined glass plate angled at 50° before sliding down. The hanging wire test determined the time it took an animal to cross a distance of 45 cm on a freely hanging narrow metal bar.

What is claimed is:

1. A method for identifying a drug candidate with activity as a neuroprotective agent, the method comprising:
 a. determining whether a compound decreases the amount of ATF4 protein by:
   i. providing a cell expressing ATF4;
   ii. contacting the cell with the compound; and
   iii. measuring the amount of ATF4 protein in the cell, wherein a decrease in the amount of ATF4 protein indicates the compound has activity as a neuroprotective agent; and
 b. identifying the compound that decreases the amount of ATF4 protein as a drug candidate.

2. The method according to claim 1, wherein the cell is in vitro.

3. The method according to claim 1, wherein the cell is ex vivo.

4. The method according to claim 1, wherein the cell is in vivo.

5. The method according to claim 1, further comprising testing the drug candidate for neuroprotective activity in a mammal.

6. The method according to claim 5, wherein the mammal is a mouse.

* * * * *